US012716089B2

(12) United States Patent
Ahn et al.

(10) Patent No.: US 12,716,089 B2
(45) Date of Patent: Aug. 25, 2026

(54) SIMULTANEOUS BACKGROUND REDUCTION AND COMPLEX STABILIZATION IN BINDING ASSAY WORKFLOWS

(71) Applicant: ILLUMINA CAMBRIDGE LIMITED, Cambridge (GB)

(72) Inventors: Keunho Ahn, San Diego, CA (US); Joseph Rokicki, San Diego, CA (US); Brittany Ann Rohrman, San Diego, CA (US); Corey M. Dambacher, La Jolla, CA (US)

(73) Assignee: ILLUMINA CAMBRIDGE LIMITED, Cambridge (GB)

( * ) Notice: Subject to any disclaimer, the term of this patent is extended or adjusted under 35 U.S.C. 154(b) by 1208 days.

(21) Appl. No.: 17/518,779

(22) Filed: Nov. 4, 2021

(65) Prior Publication Data

US 2022/0056516 A1 Feb. 24, 2022

Related U.S. Application Data

(62) Division of application No. 16/164,417, filed on Oct. 18, 2018, now Pat. No. 11,193,166.

(60) Provisional application No. 62/574,308, filed on Oct. 19, 2017.

(51) Int. Cl.
*C12Q 1/68* (2018.01)
*C12Q 1/6853* (2018.01)
*C12Q 1/6874* (2018.01)

(52) U.S. Cl.
CPC ......... *C12Q 1/6853* (2013.01); *C12Q 1/6874* (2013.01)

(58) Field of Classification Search
None
See application file for complete search history.

(56) References Cited

U.S. PATENT DOCUMENTS 5,302,509 A 4/1994 Cheeseman
5,614,365 A 3/1997 Tabor et al.
6,485,909 B1 11/2002 Hong et al.
6,720,177 B2 4/2004 Ghadiri et al.
6,828,094 B2 12/2004 Kilger et al.
6,828,159 B1 12/2004 Drexhage et al.
6,908,736 B1 6/2005 Densham
7,008,766 B1 3/2006 Densham
7,008,798 B2 3/2006 Waggoner
7,223,540 B2 5/2007 Pourmand et al.
7,264,934 B2 9/2007 Fuller
7,329,492 B2 2/2008 Hardin et al.
7,449,297 B2 11/2008 Freije et al.
7,482,120 B2 1/2009 Buzby
7,604,963 B2 10/2009 Densham
7,635,578 B2 12/2009 Ju et al.
7,713,698 B2 5/2010 Ju et al.
7,790,869 B2 9/2010 Ju et al.
7,871,771 B2 1/2011 Fuller et al.
7,939,264 B1 5/2011 Densham
8,071,755 B2 12/2011 Efcavitch et al.
8,088,575 B2 1/2012 Ju et al.
8,133,672 B2 3/2012 Bjornson et al.
8,236,532 B2 8/2012 Ronaghi et al.
8,298,792 B2 10/2012 Ju et al.
8,399,196 B2 3/2013 Hoser
8,481,266 B2 7/2013 Shao et al.
8,535,881 B2 9/2013 Schneider
8,603,741 B2 12/2013 Emig et al.
8,632,975 B2 1/2014 Vander Horn et al.
8,658,365 B2 2/2014 Bjornson et al.
8,703,461 B2 4/2014 Peris et al.
8,911,972 B2 12/2014 Chaisson et al.
8,986,930 B2 3/2015 Fedorov et al.
9,255,258 B2 2/2016 Vander Horn et al.
9,279,154 B2 3/2016 Previte et al.
9,279,155 B2 3/2016 Bjornson et al.
9,651,490 B2 5/2017 Zilles et al.
10,294,514 B2 5/2019 Iyidogan et al.
10,443,098 B2 10/2019 Vijayan et al.
10,975,427 B2 4/2021 Dambacher et al.
2004/0096853 A1 5/2004 Mayer
2006/0292583 A1 12/2006 Schneider et al.
2007/0009925 A1 1/2007 Fang et al.
2007/0148645 A1 6/2007 Hoser
2009/0061447 A1 3/2009 Schneider
(Continued)

FOREIGN PATENT DOCUMENTS

EP 1115848 A1 7/2001
WO 1990013666 A1 11/1990
(Continued)

OTHER PUBLICATIONS

U.S. Appl. No. 17/190,894, "Non-Final Office Action", Dec. 22, 2023, 14 pages.
U.S. Appl. No. 17/190,894, "Non-Final Office Action", Oct. 18, 2024, 11 pages.
CA3,050,695, "Notice of Allowance", Oct. 5, 2023, 1 page.
EP18797436.5, "Office Action", Mar. 22, 2023, 6 pages.
"5-Propargytamino-ddUTP—Cy5", Available online at https://www.jenabioscience.com/images/PDF/NU-1619-CY5.pdf, Mar. 15, 2018, 1 page.
(Continued)

*Primary Examiner* — Stephanie K Mummert
(74) *Attorney, Agent, or Firm* — Mueting Raasch Group

(57) ABSTRACT

Method and apparatus to facilitate separation of solution-phase components surrounding an immobilized multicomponent complex while stabilizing association of the components within the complex. The technique can be used for reducing background signal arising from the presence of non-complexed components harboring detectable labels, thereby enhancing signal-to-background ratios and allowing enhanced detection of the multicomponent complex.

21 Claims, 4 Drawing Sheets

(56) References Cited

U.S. PATENT DOCUMENTS

| | | | |
|---|---|---|---|
| 2010/0316999 A1 | 12/2010 | Densham | |
| 2010/0317012 A1 | 12/2010 | Ju et al. | |
| 2011/0008794 A1 | 1/2011 | Schneider | |
| 2011/0237464 A1 | 9/2011 | Cunningham et al. | |
| 2013/0165328 A1 | 6/2013 | Previte et al. | |
| 2014/0127680 A1 | 5/2014 | Emig et al. | |
| 2014/0234940 A1 | 8/2014 | Peris et al. | |
| 2015/0337366 A1 | 11/2015 | Davis et al. | |
| 2016/0010150 A1 | 1/2016 | Emig et al. | |
| 2016/0168633 A1 | 6/2016 | Previte et al. | |
| 2016/0177384 A1 | 6/2016 | Bjornson et al. | |
| 2016/0208318 A1 | 7/2016 | Vander Horn et al. | |
| 2017/0022553 A1 | 1/2017 | Vijayan et al. | |
| 2017/0191125 A1 | 7/2017 | Vijayan et al. | |
| 2017/0314064 A1* | 11/2017 | Iyidogan | C12Q 1/6809 |
| 2017/0314072 A1 | 11/2017 | Vijayan et al. | |
| 2018/0044727 A1 | 2/2018 | Vijayan et al. | |
| 2018/0187245 A1 | 7/2018 | Dambacher et al. | |
| 2018/0208983 A1 | 7/2018 | Dambacher et al. | |

FOREIGN PATENT DOCUMENTS

| | | | |
|---|---|---|---|
| WO | 0116375 | A2 | 3/2001 |
| WO | 0204680 | A2 | 1/2002 |
| WO | 2005121363 | A2 | 12/2005 |
| WO | 2009145820 | A2 | 12/2009 |
| WO | 2009145828 | A2 | 12/2009 |
| WO | 2010068884 | A2 | 6/2010 |
| WO | 2010111690 | A2 | 9/2010 |
| WO | 2011159942 | A1 | 12/2011 |
| WO | 2012166742 | A3 | 12/2012 |
| WO | 2013096692 | A1 | 6/2013 |
| WO | 2014114665 | A1 | 7/2014 |
| WO | 2016001963 | A1 | 1/2016 |
| WO | 2017014762 | A1 | 1/2017 |
| WO | 2017190012 | A1 | 11/2017 |
| WO | 2018034780 | A1 | 2/2018 |
| WO | 2018035134 | A1 | 2/2018 |
| WO | 2018136487 | A1 | 7/2018 |

OTHER PUBLICATIONS

"APCH231: Chemical Analysis Complexometric Titrations EDTA", Notes compiled by Dr. C. Southway, Available Online At: (http://cheminnerweb.ukzn.ac.za/libraries/apch231_h_govender_s_notes/apch231_edta.sflb.ashx), post date of Nov. 23, 2015, pp. 30-42.

"Ion Torrent Amplicon Sequencing", Application Note Amplicon Sequencing, Available Online at http://www.iontorrent.com/lib/images/PDFs/amplicon_application_note_040411.pdf, XP-002681382, Apr. 4, 2011, 5 pages.

U.S. Appl. No. 15/873,343, "Final Office Action", Aug. 6, 2020, 11 pages.

U.S. Appl. No. 15/873,343, "Non-Final Office Action", Mar. 20, 2020, 11 pages.

U.S. Appl. No. 15/873,343, "Non-Final Office Action", Oct. 21, 2019, 11 pages.

U.S. Appl. No. 15/873,343, "Notice of Allowance", Dec. 7, 2020, 7 pages.

U.S. Appl. No. 16/164,417, "Ex Parte Quayle Action", Aug. 19, 2021, 5 pages.

U.S. Appl. No. 16/164,417, "Non-Final Office Action", Apr. 1, 2021, 16 pages.

U.S. Appl. No. 16/164,417, "Notice of Allowance", Sep. 13, 2021, 7 pages.

Agnarsson et al., "On-Chip Modulation of Evanescent Illumination and Live-Cell Imaging With Polymer Waveguides.", Optics Express, vol. 19, Issue No. 23, Nov. 7, 2011, pp. 22929-22935.

Anker et al., "Biosensing with Plasmonic Nanosensors", Nature Materials, vol. 7, Issue No. 6, Jun. 2008, pp. 442-453.

Bandwar et al., "Peculiar 2-Aminopurine Fluorescence Monitors the Dynamics of Open Complex Formation by Bacteriophage T7 RNA Polymerase", The Journal of Biological Chemistry, vol. 275, No. 17, Apr. 27, 2001, pp. 14075-14082.

Brockman et al., "A Multistep Chemical Modification Procedure to Create DNA Arrays on Gold Surfaces for the Study of Protein—DNA Interactions with Surface Plasmon Resonance Imaging", Journal of the American Chemical Society, vol. 121, Aug. 19, 1999, pp. 8044-8051.

Brown et al., "Pre-Steady-State Kinetic Analysis of Truncated and Full-Length *Saccharomyces cerevisiae* DNA Polymerase Eta", Journal of Nucleic Acids, vol. 2010, Article ID 871939, Jul. 25, 2010, 11 pages.

CA3,079,411, "Office Action", May 17, 2021, 4 pages.

Campagnola et al., "High-Throughput Screening Identification of Poliovirus RNA-Dependent RNA Polymerase Inhibitors", Antiviral Res., vol. 91, No. 3, Sep. 2011, pp. 241-251.

Chan et al., "A General Method for Discovering Inhibitors of Protein-DNA Interactions Using Photonic Crystal Biosensors", ACS Chem Biol, vol. 3, No. 7, Jul. 18, 2008, pp. 437-448.

Chen et al., "The History and Advances of Reversible Terminators Used in New Generations of Sequencing Technology", Genomics Proteomics Bioinformatics, vol. 11, No. 1, Feb. 1, 2013, pp. 34-40.

Chin et al., "The Effect of Divalent Nickel (Ni2+) on in Vivo DNA Replication by DNA Polymerase $\alpha$1", Cancer Research, vol. 54, May 1, 1994, pp. 2337-2341.

Choi et al., "EML4-ALK Mutations in Lung Cancer that Confer Resistance to ALK Inhibitors", The New England Journal of Medicine, vol. 18, Oct. 28, 2010, pp. 1734-1739.

Concepcion et al., "Label-Free Detection of Biomolecular Interactions Using BioLayer Interferometry for Kinetic Characterization", Combinatorial Chemistry and High Throughput Screening, vol. 12, No. 8, Sep. 2009, pp. 791-800.

Crumpacker, "Mechanism of Action of Foscarnet Against Viral Polymerase", American Journal of Medicine, vol. 92, No. 2, Supplement 2A, Feb. 14, 1992, pp. 3S-7S.

Datta et al., "Salt Dependence of DNA binding by *Thermus aquaticus* and *Escherichia coli* DNA Polymerases", Journal of Biological Chemistry, vol. 278, No. 8, Feb. 21, 2003, pp. 5694-5701.

Deredge et al., "The Glutamate Effect on DNA Binding by Pol I DNA Polymerases: Osmotic Stress and the Effective Reversal of Salt Linkage", Journal of Molecular Biology, vol. 401, No. 2, Aug. 13, 2010, pp. 223-238.

Doublie et al., "An Open and Closed Case for All Polymerases", Structure, vol. 7, No. 2, Feb. 1999, pp. R31-R35.

Dunlap et al., "Use of 2-Aminopurine and Tryptophan Fluorescence as Probes in Kinetic Analyses of DNA Polymerase Beta", Biochemistry, vol. 41, No. 37, Sep. 17, 2002, pp. 11226-11235.

Dzantiev et al., "A Conformational Change in *E. coli* DNA Polymerase I (Klenow Fragment) Is Induced in the Presence of a dNTP Complementary to the Template Base in the Active Site", Biochemistry, vol. 39, No. 2, Jan. 18, 2000, pp. 356-361.

Engtrom et al., "A Label-Free Continuous Total-Internal-Reflection-Fluorescence-Based Immunosensor", Analytical Biochemistry, vol. 357, No. 2, Oct. 15, 2006, pp. 159-166.

Eriksson et al., "Pyrophosphate Analogues as Inhibitors of DNA Polymerases of Cytomegalovirus, Herpes Simplex Virus and Cellular Origin", Biochimica et Biophysica Acta, vol. 696, No. 2, Feb. 26, 1982, pp. 115-123.

Escobedo et al., "Integrated Nanohole Array Surface Plasmon Resonance Sensing Device Using a Dual-Wavelength Source", Journal of Micromechanics and Microengineering, vol. 21, No. 11, Oct. 2011, pp. 1-6.

Espinoza-Herrera et al., "Following DNA Chain Extension and Protein Conformational Changes in Crystals of a Y-Family DNA Polymerase via Raman Crystallography", Biochemistry, vol. 52, No. 29, Jul. 23, 2013, 22 pages.

Fang et al., "Genome-Wide Mapping of Methylated Adenine Residues in Pathogenic *Escherichia coli* Using Single-Molecule Real-Time Sequencing", Nature Biotechnology, vol. 30, No. 12, Dec. 2012, pp. 1232-1243.

Favicchio et al., "Fluorescence Spectroscopy and Anisotropy in the Analysis of DNA-Protein Interactions", Methods in Molecular Biology, vol. 543, Feb. 2009, pp. 589-611.

Federley, "New Insights Into the Mechanism of DNA Replication on Unmodified and Benzo[a]pyrene Modified Templates Using

(56) References Cited

OTHER PUBLICATIONS

Surface Plasmon Resonance", Wayne State University Dissertations, Paper 235., Jan. 2011, 208 pages.
Fuller et al., "The Challenges of Sequencing by Synthesis", Nature Biotechnology, vol. 27, No. 11, Nov. 2009, pp. 1013-1023.
Gralla et al., "Potassium Glutamate as a Transcriptional Inhibitor During Bacterial Osmoregulation", The EMBO Journal, vol. 25, No. 7, Apr. 5, 2006, pp. 1515-1521.
Horn et al., "EML4-ALK: Honing In on a New Target in Non-Small-Cell Lung Cancer", Journal of Clinical Oncology, vol. 27, No. 26, Sep. 10, 2009, pp. 4232-4235.
Hoshino et al., "Effect of Ultrasound on DNA Polymerase Reactions: Monitoring on a 27-MHz Quartz Crystal Microbalance", Biomacromolecules, vol. 7, No. 3, Mar. 2006, pp. 682-685.
Hutter et al., "Labeled Nucleoside Triphosphates with Reversibly Terminating Aminoalkoxyl Groups", Nucleosides, Nucleotides and Nucleic Acids, vol. 29, Nos. 11-12, Nov. 2010, pp. 879-895.
Jindal et al., "Suramin Affects DNA Synthesis in Hela Cells by Inhibition of DNA Polymerases", Cancer Research, vol. 50, Dec. 15, 1990, pp. 7754-7757.
Jochmans et al., "Indolopyridones Inhibit Human Immunodeficiency Virus Reverse Transcriptase with a Novel Mechanism of Action", Journal of Virology, vol. 80, No. 24, Dec. 2006, pp. 12283-12292.
Kaplan et al., "Photolabile Chelators for the Rapid Photorelease of Divalent Cations", Proc. Natl. Acad. Sci., vol. 85, Sep. 1988, pp. 6571-6575.
Kaushik et al., "Biochemical Analysis of Catalytically Crucial Aspartate Mutants of Human Immunodeficiency Virus Type 1 Reverse Transcriptase", Biochemistry, vol. 35, No. 36, Sep. 10, 1996, pp. 11536-11546.
Kim, "An FET-type Charge Sensor for Highly Sensitive Detection of DNA Sequence", Biosensors and Bioelectronics, vol. 20, No. 1, Jul. 30, 2004, pp. 69-74.
Klenow et al., "Effect of Monovalent Cations on the Activity of the DNA Polymerase of *Escherichia coli* B", European J. Biochem., vol. 9, 1969, pp. 133-141.
Kumar et al., "Altered Order of Substrate Binding by DNA Polymerase X from African Swine Fever Virus", Biochemistry, vol. 47, 2008, pp. 7875-7887.
Leinbach et al., "Mechanism of Phosphonoacetate Inhibition of Herpesvirus-Induced DNA Polymerase", Biochemistry, vol. 15, No. 2, 1976, pp. 426-430.
Livak et al., "Detection of Single Base Differences Using Biotinylated Nucleotides With Very Long Linker Arms", Nucleic Acids Research, vol. 20, Issue No. 18, 1992, pp. 4831-4837.
Lutz et al., "An in Vitro Screening Technique for DNA Polymerases that can Incorporate Modified Nucleotides. Pseudothymidine as a Substrate for Thermostable Polymerases", Nucleic Acids Research, vol. 27, No. 13, 1999, pp. 2792-2798.
Maga et al., "HIV-1 RT Inhibitors with a Novel Mechanism of Action: NNRTIs that Compete with the Nucleotide Substrate", Viruses, vol. 2, No. 4, 2010, pp. 880-899.
Maga et al., "Selective Interaction of the Human Immunodeficiency Virus Type 1 Reverse Transcriptase Nonnucleoside Inhibitor Efavirenz and Its Thio-Subsitituted Analog with Different Enzyme-Substrate Complexes", Antimicrobial Agents and Chemotherapy, vol. 44, No. 5, May 2000, pp. 1186-1194.
Mano, "Non-Solid Oncogenes in Solid Tumors: EML4-ALK Fusion Genes in Lung Cancer", Cancer Sci., vol. 99, No. 12, Dec. 2008, pp. 2349-2355.
Markiewicz et al., "Single-Molecule Microscopy Reveals New Insights into Nucleotide Selection by DNA Polymerase I", Nucleic Acids Research, vol. 40, No. 16, Jun. 4, 2012, pp. 7975-7984.
Masheyekhi et al., "Analysis of Read-Length Limiting Factors in Pyrosequencing Chemistry", Anal Biochem, vol. 363, Issue 3, Apr. 15, 2007, pp. 275-287.
Maxwell et al., "DNA Lesion Alters Global Conformational Dynamics of Y-family DNA Polymerase During Catalysis", The Journal of Biological Chemistry, vol. 287, No. 16, Apr. 13, 2012, pp. 13040-13047.
Nakano et al., "The Structural Stability and Catalytic Activity of DNA and RNA Oligonucleotides in the Presence of Organic Solvents", Biophysical Reviews, vol. 8, Issue No. 1, Jan. 11, 2016, pp. 11-23.
Namasivayam, "Light-Induced Molecular Cutting: Localized Reaction on a Single DNA Molecule", Anal. Chem., vol. 75, No. 16, Aug. 15, 2003, pp. 4118-4194.
Nath et al., "Label Free Colorimetric Biosensing Using Nanoparticles", Journal of Fluorescence, vol. 14, No. 4, Jul. 2004, pp. 377-389.
Nazirizadeh et al., "Low-Cost Label-Free Biosensors Using Photonic Crystals Embedded Between Crossed Polarizers", Optics Express, vol. 18, No. 18, Aug. 30, 2010, pp. 19120-19128.
Nikiforov, "Oligonucleotides Labeled With Single Fluorophores as Sensors for Deoxynucleotide Triphosphate Binding by DNA Polymerases", Analytical Biochemistry, vol. 444, 2014, pp. 60-66.
Patel, "Insights into DNA Polymerization Mechanisms from Structure and Function Analysis of HIV-1 Reverse Transcriptase", Biochemistry, vol. 34, 1995, pp. 5351-5363.
PCT/US2015/041415, "International Search Report and Written Opinion", Feb. 9, 2016, 14 pages.
PCT/US2018/014005, "International Search Report and Written Opinion", Apr. 18, 2018, 15 pages.
PCT/US2018/056507, "International Preliminary Report on Patentability", Apr. 30, 2020, 9 pages.
PCT/US2018/056507, "International Search Report and Written Opinion", Dec. 13, 2018, 13 pages.
Peletskaya et al., "Cross-Linking of the Fingers Subdomain of Human Immunodeficiency Virus Type 1 Reverse Transcriptase to Template-Primer", Journal of Virology, vol. 75, No. 19, Oct. 2001, pp. 9435-9445.
Pitta et al., "Synthesis and HIV-1 RT Inhibitory Action of Novel (4/6-substituted Benzo[d]thiazol-2-yl) Thiazolidin-4-ones. Divergence From the Non-competitive Inhibition Mechanism", Journal of Enzyme Inhibition and Medicinal Chemistry, vol. 28, No. 1, 2013, pp. 113-122.
Potapova et al., "Interaction of dNTP, Pyrophosphate and their Analogs With the dNTP-binding Sites of *E. coli* DNA Polymerase I Klenow Fragment and Human DNA Polymerase", FEBS Letters, vol. 277, Nos. 1-2, Dec. 1990, pp. 194-196.
Puttaswamy, "Optical Method for Measuring Spatial pH Change on Conductive Microelectrodes", Submitted in fulfillment for the International Master's Program (IMP) Nanomaterials and Nanotechnology, KTH, Royal Institute of Technology, Stockholm, Sweden, 2007, pp. 1-66.
Ren et al., "Inhibition of Klenow DNA Polymerase and Poly(a)-Specific Ribonuclease by Aminoglycosides", RNA, vol. 8, 2002, pp. 1393-1400.
Richard et al., "Thermal Stability Landscape for Klenow DNA Polymerase as a Function of pH and Salt Concentration", Biochimica et Biophysica Acta, vol. 1764, 2006, pp. 1546-1552.
Roettger et al., "Mismatched and Matched dNTP Incorporation by DNA Polymerase β Proceed via Analogues Kinetic Pathways", Biochemistry, vol. 47, No. 37, Aug. 22, 2008, pp. 9718-9727.
Santoso et al., "Conformational Transitions in DNA Polymerase I Revealed by Single-Molecule Fret", Proceedings of the National Academy of Sciences, vol. 107, No. 2, Jan. 12, 2010, pp. 715-720.
Schadt et al., "Modeling Kinetic Rate Variation in Third Generation DNA Sequencing Data to Detect Putative Modifications to DNA Bases", Genome Research, vol. 23, No. 1, Jan. 2013, pp. 129-141.
Schultz et al., "Single-Target Molecule Detection With Nonbleaching Multicolor Optical Immunolabels", PNAS, vol. 96, Issue No. 3, Feb. 1, 2000, pp. 996-1001.
Sen et al., "Intrinsic Fluorescence of *E. coli* RNA Polymerase as a Probe for Its Conformational Changes During Transcription Initiation", Biochem Biophys Res Commun, vol. 201, No. 2, Jun. 15, 1994, pp. 820-828.
Soda et al., "Identification of the Transforming EML4-ALK Fusion Gene in Non-Small-Cell Lung Cancer", Nature, vol. 228, Aug. 2, 2007, pp. 561-566.

(56) References Cited

OTHER PUBLICATIONS

Star et al., "Electronic Detection of Specific Protein Binding Using Nanotube FET Devices", Nano Letters, vol. 3, No. 4, Mar. 5, 2003, 5 pages.
Su et al., "Surface Plasmon Resonance Spectroscopy and Quartz Crystal Microbalance Study of Streptavidin Film Structure Effects on Biotinylated Dna Assembly and Target DNA Hybridization", Langmuir, vol. 21, No. 1, 2005, pp. 348-353.
Tsai, "Kinetics of DNA Polymerase Conformational Changes during Nucleotide Binding and Incorporation", Dissertation, May 2005, 148 pages.
Tsai et al., "Site-Specific Labeling of T7 DNA Polymerase with a Conformationally Sensitive Fluorophore and its Use in Detecting Single-Nucleotide Polymorphisms", Analytical Biochemistry, vol. 384, No. 1, Jan. 1, 2009, pp. 136-144.
Vaidyanathan et al., "Binary and Ternary Binding Affinities Between Exonuclease-Deficient Klenow Fragment (Kf-exo-) and Various Arylamine DNA Lesions Characterized by Surface Plasmon Resonance", Chemical Research in Toxicology, vol. 25, No. 8, Aug. 20, 2012, pp. 1568-1570.
Vaidyanathan et al., "Binding Kinetics of DNA-Protein Interaction Using Surface Plasmon Resonance", Protocol Exchange, May 22, 2013, 11 pages.
Vollmer et al., "Whispering-Gallery-Mode Biosensing: Label-Free Detection Down to Single Molecules", Nature Methods, vol. 5, No. 7, Jul. 2008, pp. 591-596.
Walsh et al., "Synthetic Nucleotides as Probes of DNA Polymerase Specificity", Journal of Nucleic Acids, vol. 2012, Jun. 2012, 17 pages.
Washington et al., "Human DNA Polymerase Utilizes Different Nucleotide Incorporation Mechanisms Dependent upon the Template Base", Molecular and Cellular Biology, vol. 24, No. 2, Jan. 2004, pp. 936-943.
Xia et al., "DNA Mismatch Synthesis Complexes Provide Insights into Base Selectivity of a B Family DNA Polymerase", Journal of the American Chemical Society, vol. 135, No. 1, Jan. 9, 2013, pp. 193-202.
Yuzenkova et al., "Tagetitoxin Inhibits Transcription by Stabilizing Pre-Translocated State of the Elongation Complex", Nucleic Acids Research, vol. 41, No. 20, Nov. 2013, pp. 1-9.
CA3,079,411, "Office Action", May 5, 2022, 3 pages.
CA3,050,695, "Office Action", Jun. 9, 2022, 5 pages.
CA3,079,411, "Notice of Allowance", Jun. 30, 2023, 1 page.
EP18709165.7, "Office Action", Jan. 16, 2023, 8 pages.

* cited by examiner

Fluorescence Intensity 8000 7000 6000 5000 4000 3000 2000 1000 0 dATP dGTP dCTP dTTP 1 2 3 4 5 6 7 8 9 10 11

Nucleotide Position

SIMULTANEOUS BACKGROUND REDUCTION AND COMPLEX STABILIZATION IN BINDING ASSAY WORKFLOWS

CROSS REFERENCE TO RELATED APPLICATION

This application is a divisional of U.S. application Ser. No. 16/164,417, filed Oct. 18, 2018, which is based on, and claims the benefit of, U.S. Provisional Application No. 62/574,308, filed Oct. 19, 2017, which are incorporated herein by reference in their entirety.

TECHNICAL FIELD

The present disclosure generally relates to the field of biotechnology. More specifically, the disclosure relates to compositions, methods, and systems for improving stability of reversible multicomponent complexes, for example, while depleting the system of non-complexed constituents of the multicomponent complex.

BACKGROUND

Monitoring interactions between different components in transient binding assays (e.g., reversible receptor-ligand binding interactions) has a wide range of uses in the field of biotechnology. Examples of such interactions include interactions between different proteins, between proteins and small molecules, between proteins and nucleic acids, between nucleic acids and oligonucleotides, etc. Some complexes of biological interest can include an antibody as a component (e.g., complexes formed between an antibody and an antigen or hapten), or include a cell surface receptor and a therapeutic recombinant protein. Complexes of biological interest can include two, three, or even more components or constituents.

One instance wherein reversible (i.e., transient) interactions between three different components provides valuable information concerns Sequencing By Binding™ assays that identify cognate nucleotides. Here the reversible interaction between a primed template nucleic acid, a polymerase, and a nucleotide can be monitored to identify the next correct nucleotide to be incorporated into the primed template nucleic acid. By cycling steps for monitoring binding of different test nucleotides, extensive sequence information can be obtained. Sequencing-by-binding assays can be carried out using either label-free, labeled nucleotide, or labeled polymerase platforms. These assays are stringent models for formation and maintenance of multicomponent complexes, because one readout of the assays is the accuracy with which a known nucleic acid sequence is determined.

Particularly with reference to the use of labeled polymerases and labeled nucleotides in Sequencing By Binding™ assays, background signals arising from the labeled components remaining in the presence of specific complexes undesirably may confound cognate nucleotide identification. Reduced signal-to-background ratios resulting from the presence of high levels of non-complexed reagents can mask signals representing complexes that would indicate the next correct nucleotide.

Since transient binding complexes are in dynamic equilibrium with their chemical environments, reducing the concentration of one or more components of the complex can often lead to dissociation and loss of the complex when the interaction between components is weak. For example, washing of immobilized ternary complexes to deplete free labeled reagents from the surrounding solution may facilitate specific complex detection, but may impose limitations on the timing of detection, analyses involving kinetic assessments, or undesirably complicated data processing to identify a cognate ligand, such as a cognate nucleotide. Sequencing approaches that leverage the transient nature of ternary complexes to identify the next correct nucleotide have been described in the commonly assigned published patent application identified by U.S. Pat. App. Pub. No. 2017/0022553 A1, the disclosure of which is incorporated by reference in its entirety.

It would be desirable to improve reliability of assays that detect receptor-ligand interactions, particularly those employing labeled components of the complex, by enhancing signal-to-background ratios in a manner that facilitates detection of complexes over an extended period. The present disclosure addresses this need.

SUMMARY

The present disclosure provides a method of determining whether a test ligand binds to an immobilized receptor. The method can include steps of: (a) contacting an immobilized receptor with a test ligand to form an immobilized receptor-ligand complex if the test ligand binds to the immobilized receptor, wherein the immobilized receptor-ligand complex includes the immobilized receptor in reversible association with the test ligand; (b) contacting the immobilized receptor-ligand complex that formed in step (a) with a stabilizing fluid, wherein the test ligand is substantially insoluble in the stabilizing fluid; (c) detecting the immobilized receptor-ligand complex while in contact with the stabilizing fluid; and (d) determining from the result of step (c) that the test ligand binds to the immobilized receptor.

In particular aspects, a method is provided for identifying a cognate nucleotide. The method can include steps of: (a) contacting an immobilized primed template nucleic acid molecule with a first polymerase and a first test nucleotide to form, without incorporation, an immobilized ternary complex, wherein the immobilized ternary complex includes the immobilized primed template nucleic acid molecule and the first polymerase in reversible association with the first test nucleotide; (b) contacting the immobilized ternary complex with a stabilizing fluid, wherein the first test nucleotide is substantially insoluble in the stabilizing fluid; (c) detecting the immobilized ternary complex in contact with the stabilizing fluid; and (d) identifying the cognate nucleotide from the result of step (c).

Also provided is a method of identifying a cognate nucleotide that includes steps of: (a) contacting an immobilized primed template nucleic acid molecule with a first reagent solution including a first polymerase and a first test nucleotide to form, without incorporation, an immobilized ternary complex, wherein the immobilized ternary complex comprises the immobilized primed template nucleic acid molecule, the first polymerase and the first test nucleotide in reversible association; and wherein the immobilized ternary complex is in contact with the first reagent solution and any of the first polymerase and the first test nucleotide that did not complex with the immobilized primed template nucleic acid molecule; (b) replacing the first reagent solution with a stabilizing fluid free of the first polymerase and the first test nucleotide of the first reagent solution, wherein the immobilized ternary complex is stable and does not substantially dissociate when in contact with the stabilizing fluid following the replacement; (c) detecting the immobilized ternary complex in the presence of the stabilizing fluid; and (d) identifying the cognate nucleotide from the result of step (c).

A method of detecting an immobilized ternary complex can include steps of: (a) providing a vessel having an immobilized ternary complex in a first fluid phase, wherein the immobilized ternary complex includes a primed template nucleic acid molecule, a first polymerase and a first test nucleotide, wherein the first fluid phase contains nucleotides of the same type as the first test nucleotide, and wherein the first test nucleotide is in diffusional exchange with the first fluid phase; (b) replacing at least a portion of the first fluid phase in the vessel with a second fluid phase, wherein the first test nucleotide is insoluble in the second fluid phase; and (c) detecting the immobilized ternary complex in the presence of the second fluid phase.

This disclosure also provides a vessel, that includes a ternary complex in a fluid phase, wherein the ternary complex includes a primed template nucleic acid molecule, a polymerase and a next correct nucleotide, wherein the next correct nucleotide is non-covalently bound to the primed template nucleic acid molecule, and wherein the next correct nucleotide is insoluble in the fluid phase.

BRIEF DESCRIPTION OF THE DRAWINGS

FIG. 2A shows a collection of fluorescent imaging results for a single bead. Columns represent images captured during imaging wash steps, where ternary complexes included dATP, dGTP, dCTP, and dTTP (each of these nucleotides being labeled with a fluorescent Cy5 moiety), respectively. Rows represent incremental steps that each lengthened blocked primed template nucleic acid molecules by a single nucleotide. FIG. 2B presents quantitative data obtained from the digital images of FIG. 2A. The highest magnitude signal among results from each set of four nucleotides indicates identity of the cognate nucleotide.

FIG. 3A shows fluorescent background signals obtained using air as a stabilizing fluid in an imaging wash step. FIG. 3B shows fluorescent background signals obtained using an aqueous pre-incorporation solution as a wash reagent during an imaging step.

DETAILED DESCRIPTION

Figure 1:
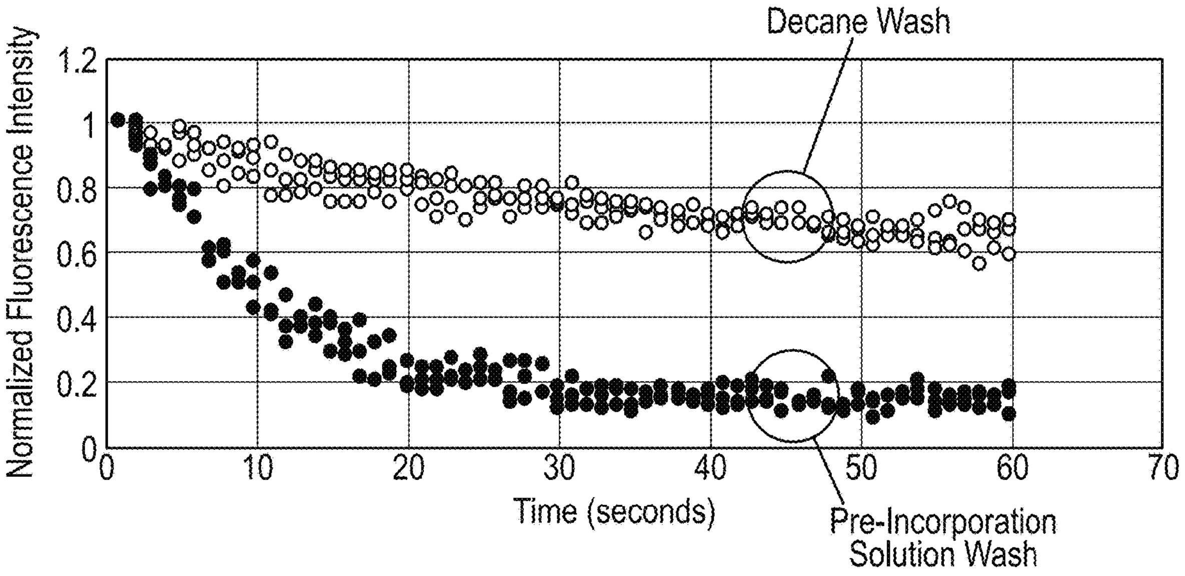
FIG. 1 is a scatter plot showing time (in seconds) on the horizontal axis and normalized fluorescent signal intensities on the vertical axis for two wash conditions following formation of ternary complexes. Trials were conducted in replicates of three for each wash condition.

Described herein is a procedure that can improve detection of transiently formed multicomponent comlexes. In some aspects, the technique is applied to systems wherein one or more of the components includes a detectable label (e.g., an exogenous fluorescent label). Using a Sequencing By Binding™ system as a model, results demonstrated that labeled polymerase sequencing, and labeled nucleotide sequencing protocols were both improved.

High concentrations of detectably labeled components are sometimes used to drive formation of transient or reversible complexes that are to be detected. Unfortunately, non-complexed reagents harboring detectable labels and remaining in the presence of the specific complexes can generate signals that confound or mask the desired detection. This is especially problematic when the signal generated by the detectable label is substantially similar irrespective of whether the labeled component (e.g., polymerase or nucleotide) is free in solution or included in a complex (e.g., a ternary complex).

The fact that nucleotide concentrations typically far exceed polymerase concentrations in binding reaction mixtures of Sequencing By Binding™ assays means that procedures employing labeled nucleotide are particularly susceptible to high backgrounds that obscure ternary complex detection. Moreover, the dynamic nature of the ternary complex (e.g., where ternary complexes are in a state of flux, forming and dissociating, and exchanging with components in their chemical environments) complicates the situation when conventional aqueous wash steps are performed to remove non-complexed reagents from the system. This is because the reversible complex that is to be detected can be unstable, and so dissociates over time (e.g., over the course of the monitoring or detection period). When the rate of loss is significant, the complex can dissociate before it can be detected.

Two technical issues impact detection of multicomponent complexes when using components that include detectable labels. First, signals originating from the labeled component can undesirably obscure detection of specific complexes due to high backgrounds. Second, conventional washing to remove one or more components from the system can promote dissociation of the reversible complexes that are to be detected. Each of these can be a liability when gathering sequencing data.

The importance of maintaining steady binding signals can be appreciated in the context of flow cell applications, where multiple images are often gathered. For example, a flow cell can include a surface area greater than a single field of view for an optical imaging system. As a consequence, an optical system may have to gather images of different parts of the flow cell by moving an optical package (e.g., lenses, cameras, illuminating apparatus, etc.) from one part to another, pausing to stabilize the system, gather an image, and repeat the process. Alternatively or additionally, the flow cell can be moved to place different sections in position for observation by an optical system. Scanning the flow cell in these ways extends processing time. If transient complexes to be monitored are unstable, then it is possible that only low-quality data—if any—will be acquired for the later images acquired in an optical scanning step. As set forth herein, this problem can be overcome by stabilizing complexes under a condition that permits acquisition of data with high signal-to-background ratios.

As detailed below, simultaneously stabilizing ternary complexes while removing non-complexed components (e.g., excess labeled polymerase, or labeled nucleotide remaining in solution) from the binding reaction mixture can be used to overcome this problem. This can involve immobilizing the ternary complex to a solid support, and then flushing or washing the system using a fluid in which the labeled reagent(s) are substantially insoluble. By this approach, components of preformed multicomponent complexes cannot substantially partition into the stabilizing fluid used in the imaging wash, or flush step, and so association of the different components or constituents of the complex is maintained. While not wishing to be limited by any particular theory of operation, it is possible that multicomponent complexes can be precipitated or encapsulated in place to maintain integrity of the complex. Whether or not structural interaction between components of the ternary complex remain in native or precipitated form following contact with the stabilizing fluid, both the polymerase and the nucleotide remain localized with the immobilized primed template nucleic acid. For simplicity, this aggregation of the immobilized primed template nucleic acid molecule, the polymerase and the cognate nucleotide is generally referred to herein using the term, "ternary complex."

Advantageously, signals associated with immobilized complexes can be highly stable when using the disclosed technique. By this it is meant that complexes can remain detectable over the course of at least 10 seconds, at least 30 seconds, and even at least 10 minutes. These stability ranges can easily exceed the time needed to make a measurement that would identify the labeled component of the complex. For example, this extent of stabilization is sufficient to permit imaging of multiple different parts or sections of a flow cell using a "tiling" approach, where an aggregated collection of imaged sections represents the flow cell surface.

The compositions, methods, and systems disclosed herein can be used for detecting the presence of a ligand for a receptor that is immobilized (i.e., an "immobilized receptor"). Ligands for receptors (or vice versa) can be detected, identified or even discovered by the techniques herein. Associations between ligands and receptors of interest can be reversible binding interactions (e.g., non-covalent interactions). Advantageously, detectably labeled ligands that remain in the solution phase, and that do not complex with immobilized receptors to form immobilized receptor-ligand complexes, can be removed from the vicinity of immobilized receptor-ligand complexes using stabilizing fluids. This can facilitate detection of specific complexes including the immobilized receptor and its specific ligand binding partner by reducing non-specific background signals. Ligands in accordance with the disclosure are substantially insoluble in the stabilizing fluid, and so do not substantially partition into the stabilizing fluid from the immobilized receptor-ligand complex. By this approach, even high concentrations of detectably labeled ligands can be employed to drive formation of immobilized receptor-ligand complexes without increasing background signals to a point where specific interactions are obscured or rendered undetectable.

Techniques that simultaneously reduce background signal detection while stabilizing binding complexes are illustrated herein using a stringent system designed for DNA sequencing, via a Sequencing By Binding™ technique. Here the next correct nucleotide (i.e., a "cognate" of the next template nucleotide) to be incorporated into the primer strand of a primed template nucleic acid is identified by formation of a three-component complex without necessarily incorporating that nucleotide. This multicomponent complex can include a primed template nucleic acid molecule, a polymerase, and the next correct nucleotide, can be used to identify the next correct nucleotide.

Unless defined otherwise, all technical and scientific terms used herein have the same meaning as is commonly understood by one of ordinary skill in the art. For clarity, the following specific terms have the specified meanings. Other terms are defined in other sections herein.

The singular forms "a" "an" and "the" include plural referents unless the context clearly dictates otherwise. Approximating language, as used in the description and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the compositions, apparatus, or methods of the present disclosure. At the very least, each numerical parameter should at least be construed in light of the number of reported significant digits and by applying ordinary rounding techniques.

As used herein, a "ligand" is a molecule that binds to another molecule (or complex of molecules), such as a receptor. Example ligands include peptides or polypeptides, antibodies, hormones, small molecule drugs, nucleotides, etc. Ligands can be naturally occurring or synthetic molecules. The combination of a ligand bound to a receptor by a reversible association can be termed a "receptor-ligand complex."

As used herein, a "receptor" is a chemical group or molecule (such as a protein) that has an affinity for a specific chemical group or molecule. Example receptors include proteins on or isolated from the surface or interior of a cell, nucleic acids that are either single- or double-stranded, etc. A primed template nucleic acid molecule bound by a polymerase can serve as a receptor for a cognate nucleotide ligand. "Receptor" embraces naturally occurring and synthetic molecules. The combination of a receptor bound to a ligand by a reversible association can be termed a "receptor-ligand complex."

As used herein, a "fluid" is substance, as a liquid or a gas, that is capable of flowing and that changes its shape to fill a vessel. In many conditions, a fluid will change shape at a steady rate when acted upon by a force tending to change its shape.

As used herein, a "stabilizing fluid" is a fluid that can contact a ternary complex without substantially promoting decomposition, dissolution, or loss of polymerase or nucleotide from the complex. Neither nucleotides nor polymerases are substantially soluble in the stabilizing fluids, and so components (e.g., nucleotide and polymerase) of an immobilized ternary complex do not partition into the bulk phase of a stabilizing fluid. For example, an immobilized ternary complex formed in the presence of a reagent solution that includes a polymerase and cognate nucleotide may not partition into the bulk phase of a stabilizing fluid that replaces the reagent solution (e.g., by fluid flow through a flow cell), or substitutes in its place. Examples of stabilizing fluids include, without limitation: air, gas, oils (e.g. silicone oils, mineral oils, carbonate oils), alcohols (e.g., ethanol and isopropanol), hydrocarbons such as alkane hydrocarbons (e.g. decane, heptane or hexane), and alcohol-containing solutions that do not substantially solubilize polymerases or nucleotides. Gases that are inert to reagents and other components used in a reaction of the present disclosure can be particularly useful including, for example, nitrogen, argon, helium or neon.

As used herein, a "non-aqueous fluid" is a fluid that is substantially free of or free of water. For example, the non-aqueous fluid is free of water when located in isolation from other components or in its original shipping container or vessel. When used in the provided methods, e.g., in combination with a step including a wash solution, the non-aqueous fluid may contact water or even include residual water molecules but still be substantially free of water. Examples of non-aqueous fluids would be air, hydrocarbons, and oils (e.g., silicone oil or mineral oil).

As used herein, "miscible" is a term describing two fluids that form a homogeneous mixture or solution when added together.

As used herein, "immiscible" is a term describing two fluids or liquids (including, for example, one fluid that is a liquid and a second that is not) that do not form a homogenous substance when mixed together under particular conditions. One fluid may be soluble in another fluid at low concentrations such that the fluid is immiscible with the other fluid over a solubility limit. For example, air is immiscible with water or other aqueous liquids above a solubility limit defined by Henry's Law. Likewise, silicone oil (e.g., having a polymer backbone of alternating silicon and oxygen atoms) is immiscible with water and aqueous liquids (e.g., liquids containing nucleotides and polymerases) when present in an amount above solubility limits. One useful category of fluids useful for performing washes or flush steps includes "water-immiscible fluids."

As used herein, "equilibrium" refers to a state of balance due to the equal action of opposing forces (e.g., equal, opposite rates). For example, a ternary complex formed between a polymerase, cognate nucleotide and immobilized primed template nucleic acid is in "equilibrium" with unbound polymerase, cognate nucleotide and immobilized primed template nucleic acid when the rate of formation of the ternary complex is balanced by the rate of its dissolution.

A Sequencing By Binding technique is a sequencing technique wherein specific binding of a polymerase to a primed template nucleic acid is used for identifying the next correct nucleotide to be incorporated into the primer strand of the primed template nucleic acid. The specific binding interaction precedes chemical incorporation of the nucleotide into the primer strand, and so identification of the next correct nucleotide can take place either without or before incorporation of the next correct nucleotide.

As used herein, "nucleic acid" or "oligonucleotide" or "polynucleotide" means at least two nucleotides covalently linked together. Thus, the terms include, but are not limited to, DNA, RNA, analogs (e.g., derivatives) thereof or any combination thereof, that can be acted upon by a polymerizing enzyme during nucleic acid synthesis. The term includes single-, double-, or multiple-stranded DNA, RNA and analogs (e.g., derivatives) thereof. Double-stranded nucleic acids advantageously can minimize secondary structures that may hinder nucleic acid synthesis. A double stranded nucleic acid may possess a nick or a single-stranded gap. A nucleic acid may represent a single, plural, or clonally amplified population of nucleic acid molecules.

As used herein, the "next correct nucleotide" is the nucleotide having a base complementary to the base of the next template nucleotide. The next correct nucleotide can be referred to as a "cognate" of the next template nucleotide and vice versa. The next correct nucleotide will hybridize at the 3'-end of a primer to complement the next template nucleotide. The next correct nucleotide can be, but need not necessarily be, capable of being incorporated at the 3' end of the primer. For example, the next correct nucleotide can be a member of a ternary complex that will complete an incorporation reaction or, alternatively, the next correct nucleotide can be a member of a stabilized ternary complex that does not catalyze an incorporation reaction. The next correct nucleotide can be a nucleotide analog. A nucleotide having a base that is not complementary to the next template base is referred to as an "incorrect" (or "non-cognate") nucleotide. The next correct nucleotide, when participating in a ternary complex, is non-covalently bound to the primed template nucleic acid of the ternary complex.

As used herein, the "next template nucleotide" refers to the nucleotide in a template nucleic acid that is located immediately 5' of the base in the template that is hybridized to the 3'-end of a hybridized primer. The base moiety of the next template nucleotide is referred to as the "next template base".

As used herein, a "template nucleic acid" is a nucleic acid to be acted upon (e.g., amplified, detected or sequenced) using a method or composition disclosed herein.

As used herein, a "primed template nucleic acid" (or alternatively, "primed template nucleic acid molecule") is a template nucleic acid primed with (i.e., hybridized to) a primer, wherein the primer is an oligonucleotide having a 3'-end with a sequence complementary to a portion of the template nucleic acid. The primer can optionally have a free 5'-end (e.g., the primer being noncovalently associated with the template) or the primer can be continuous with the template (e.g., via a hairpin structure). The primed template nucleic acid includes the complementary primer and the template nucleic acid to which it is bound. Unless explicitly stated, the primer of the primed template nucleic acid can have either a 3'-end that is extendible by a polymerase, or a 3'-end that is blocked from extension.

As used herein, a "blocked primed template nucleic acid" (or alternatively, "blocked primed template nucleic acid molecule") is a primed template nucleic acid modified to preclude or prevent phosphodiester bond formation at the 3'-end of the primer. Blocking may be accomplished, for example, by chemical modification with a blocking group at either the 3' or 2' position of the five-carbon sugar at the 3' terminus of the primer. Alternatively, or in addition, chemical modifications that preclude or prevent phosphodiester bond formation may also be made to the nitrogenous base of a nucleotide. Reversible terminator nucleotide analogs including each of these types of blocking groups will be familiar to those having an ordinary level of skill in the art. Incorporation of these analogs at the 3' terminus of a primer of a primed template nucleic acid molecule results in a blocked primed template nucleic acid molecule. The blocked primed template nucleic acid includes the complementary primer, blocked from extension at its 3'-end, and the template nucleic acid to which it is bound.

As used herein, a "nucleotide" is a molecule that includes a nitrogenous base, a five-carbon sugar (ribose or deoxyribose), and at least one phosphate group. The term embraces, but is not limited to, ribonucleotides, deoxyribonucleotides, nucleotides modified to include exogenous labels or reversible terminators, and nucleotide analogs.

As used herein, a "native" nucleotide refers to a naturally occurring nucleotide that does not include an exogenous label (e.g., a fluorescent dye, or other label) or chemical modification such as may characterize a non-natural nucleotide analog. Examples of native nucleotides useful for carrying out the Sequencing By Binding™ procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate).

As used herein, a "non-natural nucleotide analog" has one or more modifications, such as chemical moieties, which replace, remove and/or modify any of the components (e.g., nitrogenous base, five-carbon sugar, or phosphate group(s)) of a native nucleotide. Non-natural nucleotide analogs may be either incorporable or non-incorporable by a polymerase in a nucleic acid polymerization reaction. Optionally, the 3'-OH group of a non-natural nucleotide analog is modified or replaced with another moiety. The other moiety may be a reversible or irreversible terminator of polymerase extension.

The base of a nucleotide, whether it be a native nucleotide or non-natural nucleotide analog, may be any of adenine, cytosine, guanine, thymine, or uracil, or analogs thereof. Optionally, a nucleotide has an inosine, xanthine, hypoxanthine, isocytosine, isoguanine, nitropyrrole (including 3-nitropyrrole) or nitroindole (including 5-nitroindole) base. Nucleotides may include, but are not limited to, ATP, UTP, CTP, GTP, ADP, UDP, CDP, GDP, AMP, UMP, CMP, GMP, dATP, dTTP, dUTP, dCTP, dGTP, dADP, dTDP, dCDP, dGDP, dAMP, dTMP, dCMP, and dGMP. Nucleotides may also contain terminating inhibitors of DNA polymerase, dideoxynucleotides or 2',3' dideoxynucleotides, which are abbreviated as ddNTPs (ddGTP, ddATP, ddTTP, ddUTP and ddCTP).

As used herein, a "blocking moiety," when used in reference to a non-natural nucleotide analog, is a part of the analog that inhibits or prevents the 3' oxygen of the analog from forming a covalent linkage to a second nucleotide (e.g., via the 3' oxygen of the analog when it is present at the 3' end of a primer) during the incorporation step of a nucleic acid polymerization reaction. The blocking moiety of a "reversible terminator" nucleotide can be removed from a non-natural nucleotide analog to allow for nucleotide incorporation. Such a blocking moiety is referred to herein as a "reversible terminator moiety." Exemplary reversible terminator moieties are set forth in U.S. Pat Nos. 7,427,673; 7,414,116; and 7,057,026 and PCT publications WO 91/06678 and WO 07/123744, each of which is incorporated by reference in its entirety.

As used herein, a "test nucleotide" is a nucleotide being investigated for its ability to participate in formation of a ternary complex that further includes a primed template nucleic acid and a polymerase.

As used herein, "polymerase" refers to a protein or other molecule that forms a ternary complex with a cognate nucleotide and primed template nucleic acid (or blocked primed template nucleic acid) including but not limited to, DNA polymerase, RNA polymerase, reverse transcriptase, primase and transferase. Typically, the polymerase includes one or more active sites at which nucleotide binding may occur. Optionally a polymerase includes one or more active sites at which catalysis of nucleotide polymerization may occur. Optionally a polymerase lacks catalytic nucleotide polymerization function, for example, due to a modification such as a mutation or chemical modification. Alternatively, a polymerase may catalyze the polymerization of nucleotides to the 3'-end of a primer bound to its complementary nucleic acid strand. For example, a polymerase catalyzes the addition of a next correct nucleotide to the 3'-oxygen of the primer via a phosphodiester bond, thereby chemically incorporating the nucleotide into the primer. Optionally, the polymerase used in the provided methods is a processive polymerase. Optionally, the polymerase used in the provided methods is a distributive polymerase.

As used herein, a "variant" of a polypeptide reference sequence is a form or version of the polypeptide sequence that differs in some respect. Variants can differ in amino acid sequence and can include, for example, amino acid substitutions, additions (e.g., insertions, and extensions of termini), and deletions. A variant of a polypeptide reference sequence can include amino acid substitutions and/or internal additions and/or deletions and/or additional amino acids at one or both termini of the reference sequence.

As used herein, a "salt providing monovalent cation" is an ionic compound that dissociates in aqueous solution to produce cations having a single positive charge. For example, the cations can be metal cations where the oxidation state is +1.

As used herein, "a glutamate salt" is an ionic compound that dissociates in aqueous solution to produce glutamate anions.

As used herein, "monitoring" (or sometimes "measuring"), when used in reference to a molecular binding event, refers to a process of detecting a measurable interaction or binding between two molecular species. For example, monitoring may involve detecting measurable interactions between a polymerase and primed template nucleic acid (or blocked primed template nucleic acid), typically at various points throughout a procedure. Monitoring can be intermittent (e.g., periodic) or continuous (e.g., without interruption), and can involve acquisition of quantitative results. Monitoring can be carried out by detecting multiple signals over a period of time during a binding event or, alternatively, by detecting signal(s) at a single time point during or after a binding event.

As used herein, "contacting," when used in reference to chemical reagents, refers to the mixing together of reagents (e.g., mixing an immobilized template nucleic acid and either a buffered solution that includes a polymerase, or the combination of a polymerase and a test nucleotide) so that a physical binding reaction or a chemical reaction may take place.

As used herein, "incorporating" or "chemically incorporating," when used in reference to a primed template and nucleotide, refers to the process of joining a nucleotide to a primer by formation of a phosphodiester bond. In particular aspects, the nucleotide is a cognate of the next base of a template to which the primer is hybridized.

As used herein, "extension" refers to the process after an oligonucleotide primer and a template nucleic acid have annealed to one another, wherein one or more nucleotides is added at the 3'-end of the primer. A polymerase enzyme can catalyze addition of a single nucleotide to a primer. An oligonucleotide, which contains multiple nucleotides, can be added to a primer by a ligase enzyme. A nucleotide or oligonucleotide that is added to a nucleic acid by extension is said to be "incorporated" into the nucleic acid. Accordingly, the term "incorporating" can be used to refer to the process of joining a nucleotide to the 3'-end of a primer by formation of a phosphodiester bond.

As used herein, a "binary complex" is a complex between a polymerase and a primed template nucleic acid (e.g. blocked primed template nucleic acid), where the complex does not include a nucleotide molecule such as the next correct nucleotide.

As used herein, a "ternary complex" is a complex between a polymerase, a primed template nucleic acid (e.g., blocked primed template nucleic acid), and the next correct nucleotide positioned immediately downstream of the primer and complementary to the template strand of the primed template nucleic acid (e.g., the blocked primed template nucleic acid). The primed template nucleic acid can include, for example, a primer with a free 3'-OH or a blocked primer (e.g., a primer with a chemical modification on the base or the sugar moiety of the 3' terminal nucleotide, where the modification precludes enzymatic phosphodiester bond formation). The term "stabilized ternary complex" means a ternary complex having promoted or prolonged existence or a ternary complex for which disruption has been inhibited. Generally, stabilization of the ternary complex prevents covalent incorporation of the nucleotide component of the ternary complex into the primed nucleic acid component of the ternary complex.

As used herein, a "catalytic metal ion" refers to a metal ion that facilitates phosphodiester bond formation between the 3'-OH of a nucleic acid (e.g., a primer) and the phosphate of an incoming nucleotide by a polymerase. A "divalent catalytic metal cation" is a catalytic metal ion having a valence of two. Catalytic metal ions can be present at sufficiently low concentrations to stabilize formation of a complex between a polymerase, a nucleotide, and a primed template nucleic acid, referred to as non-catalytic concentrations of a metal ion. Catalytic concentrations of a metal ion refer to the amount of a metal ion sufficient for polymerases to catalyze the reaction between the 3'-OH group of a nucleic acid (e.g., a primer) and the phosphate group of an incoming nucleotide.

As used herein, a "non-catalytic metal ion" refers to a metal ion that, when in the presence of a polymerase enzyme, does not facilitate phosphodiester bond formation needed for chemical incorporation of a nucleotide into a primer. Typically, the non-catalytic metal ion is a cation. A non-catalytic metal ion may inhibit phosphodiester bond formation by a polymerase, and so may stabilize a ternary complex by preventing nucleotide incorporation. Non-catalytic metal ions may interact with polymerases, for example, via competitive binding compared to catalytic metal ions. A "divalent non-catalytic metal ion" is a non-catalytic metal ion having a valence of two. Examples of divalent non-catalytic metal ions include, but are not limited to, $Ca^{2+}$, $Zn^{2+}$, $Co^{2+}$, $Ni^{2+}$, and $Sr^{2+}$. The trivalent $E^{3+}$ and $Tb^{3+}$ ions are non-catalytic metal ions having a valence of three.

As used herein an "exogenous label" refers to a detectable chemical moiety of a molecule (e.g., a sequencing reagent) that is not present in a natural analog of the molecule (e.g., sequencing reagent), such as a non-naturally occurring label present on a synthetic nucleotide analog or a synthetic polymerase analog (e.g., a DNA polymerase). While a native dNTP may have a characteristic limited fluorescence profile, the native dNTP does not include any added colorimetric or fluorescent moiety. Conversely, a dATP (2'-deoxyadenosine-5'-triphosphate) molecule modified to include a chemical linker and fluorescent moiety attached to the gamma phosphate would be said to include an exogenous label because the attached chemical components are not ordinarily a part of the nucleotide. Of course, chemical modifications to add detectable labels to nucleotide bases also would be considered exogenous labels. Likewise, a DNA polymerase modified to include a fluorescent dye (e.g., by attachment to a cys residue that is part of the primary sequence of the enzyme) also would be said to include an exogenous label because the label is not ordinarily a part of the polymerase.

As used herein, "unlabeled" refers to a molecular species free of added or exogenous label(s) or tag(s). Of course, unlabeled nucleotides will not include either of an exogenous fluorescent label, or an exogenous Raman scattering tag. A native nucleotide is another example of an unlabeled molecular species. An unlabeled molecular species can exclude one or more of the labels set forth herein or otherwise known in the art relevant to nucleic acid sequencing or analytical biochemistry.

As used herein, the term "solid support" refers to a rigid substrate that is insoluble in aqueous liquid. The substrate can be non-porous or porous. The substrate can optionally be capable of taking up a liquid (e.g., due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers.

As used herein, a "flow cell" is a reaction chamber that includes one or more channels that direct fluid in a predetermined manner to conduct a desired reaction. The flow cell can be coupled to a detector such that a reaction occurring in the reaction chamber can be observed. For example, a flow cell can contain primed template nucleic acid molecules, for example, tethered to a solid support, to which nucleotides and ancillary reagents are iteratively applied and washed away. The flow cell can include a transparent material that permits the sample to be imaged after a desired reaction occurs. For example, a flow cell can include a glass or plastic slide containing small fluidic channels through which polymerases, dNTPs and buffers can be pumped. The glass or plastic inside the channels can be decorated with one or more primed template nucleic acid molecules to be sequenced. An external imaging system can be positioned to detect the molecules on the surface of the glass or plastic. Reagent exchange in a flow cell is accomplished by pumping, drawing, or otherwise "flowing" different liquid reagents through the flow cell. Exemplary flow cells, methods for their manufacture and methods for their use are described in US Pat. App. Publ. Nos. 2010/0111768 Al or 2012/0270305 A1; or WO 05/065814, each of which is incorporated by reference herein in its entirety.

As used herein, a "reaction vessel" is a container that isolates one reaction (e.g., a binding reaction; an incorporation reaction; etc.) from another, or that provides a space in which a reaction can take place. Non-limiting examples of reaction vessels useful in connection with the disclosed technique include: flow cells, wells of a multiwell plate; microscope slides; tubes (e.g., capillary tubes); etc. Features to be monitored during binding and/or incorporation reactions can be contained within the reaction vessel.

As used herein, a "kit" is a packaged unit containing one or more components that can be used for performing detection and/or sequencing reactions using an engineered DNA polymerase, as disclosed herein. Typical kits may include packaged combinations, in one or more containers or vials, of reagents to be used in the procedure.

As used herein, the term "diffusional exchange," when used in reference to a member of a binding complex, refers to the ability of the member to move in or through a fluid to associate and dissociate from another member of the complex. Diffusional exchange can occur when there are no barriers that prevent the members from interacting with each other to form a complex. However, diffusional exchange is understood to exist even if diffusion is retarded, reduced or altered so long as access is not absolutely prevented.

As used herein, the term "transport" refers to movement of a molecule through a fluid. The term can include passive transport such as movement of molecules along their concentration gradient (e.g., passive diffusion). The term can also include active transport whereby molecules can move along their concentration gradient or against their concentration gradient. Thus, transport can include applying energy to move one or more molecule in a desired direction or to a desired location such as an amplification site. Transport can occur, for example, within a single fluid phase, between a solid phase and fluid phase, or between a first fluid phase and a second fluid phase.

As used herein, a complex that is "transient" in nature, or that forms "transiently," is a complex that is capable of dissociating at least one component of the complex. For example, the complex can be in dynamic equilibrium with one or more non-complexed components in its environment so that the complex is in a state of formation and dissociation at the same time. Thus, formation of the complex can be considered "reversible."

As used herein, "reversible association" when used in reference to a multicomponent complex (e.g., a binary complex or a ternary complex) means that the complex is in a state of formation and dissociation. When the quantity of the multicomponent complex is constant, the rate of formation and the rate of dissociation are balanced and the complex is in equilibrium with the chemical components of its surroundings.

As used herein, a "complex" is a molecular entity formed by non-covalent association involving two or more component molecular entities (e.g., a polymerase and either a primed template nucleic acid molecule or blocked primed template nucleic acid molecule).

As used herein, "imaging" refers to a process for obtaining a representation of a sample or a portion thereof. The process may involve acquisition of optical data, such as the relative location of a feature undergoing analysis, and intensity of an optical signal produced at the position of the feature.

As used herein, an "imaging wash" step refers to a process that involves introducing a stabilizing fluid to a vessel or solid support that has one or more multi-component complexes (e.g., binary or ternary complexes), and imaging the complexes while they are in contact with the stabilizing fluid or otherwise in the presence of the stabilizing fluid. The process can take place within a flow cell, within a well of a multiwell plate, or in or on any other vessel appropriate for containing the complexes. In some aspects, the imaging wash step is conducted using a flow cell.

As used herein, the term "replace," when used in reference to two fluids, means removing most or all of a first fluid and adding a second fluid in place of the removed first fluid. For example, at least 75%, 80%, 90%, 95%, 99%, 99.9% or 100% of the first fluid can be removed.

As used herein, "dynamic equilibrium" refers to a condition that exists when a reversible reaction ceases to change its ratio of products/reactants. If the rate of a forward reaction (e.g., ternary complex formation) is balanced by the rate of a reverse reaction (e.g., ternary complex dissociation), then there is no net change.

As used herein, an "intercalating dye" is a chemical compound with high affinity for DNA, where the compound binds or inserts between the planar base pairs of a nucleic acid double helix and changes its spectral properties as a consequence. In the context of the present disclosure, the term further embraces minor groove binding dyes, and major groove binding dyes that change fluorescent properties, for example by increasing fluorescence emission, because of the binding.

As used herein, "energy transfer relationship" refers to a relationship between two labels (e.g., a "donor" and an "acceptor") held sufficiently close that energy emitted by one label can be received or absorbed by the other label. The "donor" is the moiety that initially absorbs the energy, and the "acceptor" is the moiety to which the energy is subsequently transferred. An "energy transfer partner" refers to one member of the pair of interactive labels (i.e., the donor and acceptor), without specifying whether the member functions as the donor or acceptor.

As used herein, "FRET" (i.e., fluorescence resonance energy transfer) refers to the distance-dependent radiationless transmission of energy quanta from the site of absorption to the site of its utilization in a molecule or system of molecules by resonance interaction between chromophores.

As used herein, "available for polymerization" refers to a molecular species (e.g., a primed template nucleic acid) that is competent for participating as a substrate in a polymerization reaction. Removing a reversible terminator moiety from the nucleotide at the 3'-end of a blocked primed template nucleic acid molecule (e.g., in a "deblocking" reaction) renders the resulting molecule "available for polymerization" if that molecule can participate in an enzymatic reaction involving phosphodiester bond formation with a cognate nucleotide.

The terms "cycle" or "round," when used in reference to a sequencing procedure, refer to the portion of a sequencing run that is repeated to indicate the presence of a nucleotide. Typically, a cycle or round includes several steps such as steps for delivery of reagents, washing away unreacted reagents and detection of signals indicative of changes occurring in response to added reagents.

As used herein, "destabilize" and its grammatical variants means to cause something to be unable to continue existing or working in its usual way. "Destabilizing" a ternary complex refers to the process of promoting dissolution or breakdown of the ternary complex (e.g., separating nucleotide and/or polymerase components of the ternary complex from the primed template nucleic acid molecule component).

The aspects set forth below and recited in the claims can be understood in view of the above definitions.

A method of the present disclosure can be used to identify one or more nucleotides in a template nucleic acid. In some aspects, the methods include one or more steps of a Sequencing By Binding™ (SBB™) reaction. Particularly useful SBB™ reactions are described in commonly owned US Pat. App. Pub. No. 2017/0022553 A1; US Pat. App. Pub. No. 2018/0044727 A1 which is the publication of U.S. patent application Ser. No. 15/677,870 and claims priority to U.S. patent application Ser. Nos. 62/447,319; US Pat. App. Pub. No. 2018/0187245 A1 which is the publication of U.S. patent application Ser. No. 15/851,383 and claims priority to 62/440,624; or US Pat. App. Pub. No. 2018/0208983 A1 which is the publication of U.S. patent application Ser. No. 15/873,343 and claims priority to 62/450,397, each of which is incorporated by reference in its entirety. Generally, methods for determining the sequence of a template nucleic acid molecule can be based on formation of a ternary complex (between polymerase, primed nucleic acid and cognate nucleotide) under specified conditions. The method can include an examination phase followed by a nucleotide incorporation phase.

An examination phase of an SBB™ reaction can be carried out in a flow cell (or other vessel), the flow cell containing at least one template nucleic acid molecule primed with a primer by delivering to the flow cell reagents to form a first reaction mixture. The reaction mixture can include the primed template nucleic acid, a polymerase and at least one nucleotide type. Interaction of polymerase and a nucleotide with the primed template nucleic acid molecule(s) can be observed under conditions where the nucleotide is not covalently added to the primer(s); and the next base in each template nucleic acid can be identified using the observed interaction of the polymerase and nucleotide with the primed template nucleic acid molecule(s). The interaction between the primed template, polymerase and nucleotide can be detected in a variety of schemes. For example, the nucleotides can contain a detectable label. Each nucleotide can have a distinguishable label with respect to other nucleotides. Alternatively, some or all of the different nucleotide types can have the same label and the nucleotide types can be distinguished based on separate deliveries of different nucleotide types to the flow cell. In some aspects, the polymerase can be labeled. Polymerases that are associated with different nucleotide types can have unique labels that distinguish the type of nucleotide to which they are associated. Alternatively, polymerases can have similar labels and the different nucleotide types can be distinguished based on separate deliveries of different nucleotide types to the flow cell. Detection can be carried out by scanning the flow cell using a method or stabilizing fluid set forth herein.

During an examination phase that is used to detect a ternary complex, discrimination between correct and incorrect nucleotides can be facilitated by stabilizing the ternary complex. A variety of conditions and reagents can be useful. For example, the primer can contain a reversible blocking moiety that prevents covalent attachment of nucleotide; and/or cofactors that are required for extension, such as divalent metal ions, can be absent; and/or inhibitory divalent cations that inhibit polymerase-based primer extension can be present; and/or the polymerase that is present in the examination phase can have a chemical modification and/or mutation that inhibits primer extension; and/or the nucleotides can have chemical modifications that inhibit incorporation, such as 5' modifications that remove or alter the native triphosphate moiety. The examination phase can include scanning of the flow cell using a method or stabilizing fluid set forth herein.

An extension phase can follow examination in an SBB™ protocol. Extension, whether carried out in an SBB™ protocol or other process can be carried out by creating conditions (e.g. in a flow cell) where a nucleotide can be added to the primer on each template nucleic acid molecule. In some aspects, this involves removal of reagents used in an examination phase and replacing them with reagents that facilitate extension. For example, examination reagents can be replaced with a polymerase and nucleotide(s) that are capable of extension. Alternatively, one or more reagents can be added to an examination phase reaction to create extension conditions. For example, catalytic divalent cations can be added to an examination mixture that was deficient in the cations, and/or polymerase inhibitors can be removed or disabled, and/or extension competent nucleotides can be added, and/or a deblocking reagent can be added to render primer(s) extension competent, and/or extension competent polymerase can be added.

Steps for a complex forming reaction, such as the above sequencing methods, can be carried out cyclically. For example, examination and extension steps of an SBB method can be repeated such that in each cycle a single next correct nucleotide is examined (i.e., the next correct nucleotide being a nucleotide that correctly binds to the nucleotide in a template nucleic acid that is located immediately 5' of the base in the template that is hybridized to the 3'-end of the hybridized primer) and, subsequently, a single next correct nucleotide is added to the primer.

Any number of cycles of a sequencing method set forth herein can be carried out including, for example, at least 1, 2, 5, 10, 20, 25, 30, 40, 50, 75, 100, 150 or more cycles. Alternatively, or additionally, no more than 150, 100, 75, 50, 40, 30, 25, 20, 10, 5, 2 or 1 cycles are carried out.

Nucleic acid template(s), to be sequenced or otherwise used in a method set forth herein, can be added to a vessel using any of a variety of known methods. In some aspects, a single nucleic acid molecule is to be sequenced or otherwise used. The nucleic acid molecule can be delivered to a vessel and can optionally be attached to a surface in the vessel. In some aspects, the molecule is detected at single molecule resolution (e.g., single molecule sequencing). Alternatively, multiple copies of the nucleic acid can be made and the copies can be sequenced or detected as an ensemble. For example, the nucleic acid can be amplified on a surface (e.g., on the inner wall of a flow cell) using techniques set forth in further detail below.

In multiplex aspects, a variety of different nucleic acid molecules (i.e., a population having a variety of different sequences) are used. The molecules can optionally be attached to a surface in a vessel. The nucleic acids can be attached at unique sites on the surface and single nucleic acid molecules that are spatially distinguishable one from the other can be processed in parallel. Alternatively, the nucleic acids can be amplified on the surface to produce a plurality of surface attached ensembles. The ensembles can be spatially distinguishable and processed in parallel. Each ensemble can be clonal, containing multiple copies of a particular sequence. Alternatively, an ensemble can have a low level of other sequences, such as variants arising from amplification errors or alternative sequences arising from contaminant templates. Sufficiently low levels of other sequences can be accommodated, for example, where signal to noise arising from the ensemble as a whole is above a desired detection threshold.

A method set forth herein can use any of a variety of amplification techniques in a vessel. Exemplary techniques that can be used include, but are not limited to, polymerase chain reaction (PCR), rolling circle amplification (RCA), multiple displacement amplification (MDA), bridge amplification, or random prime amplification (RPA). In particular aspects, one or more primers used for amplification can be attached to a surface in a vessel. Methods that result in one or more sites on a solid support, where each site is attached to multiple copies of a particular nucleic acid template, can be referred to as “clustering” methods.

One or both primers used for amplification can be attached to a surface, for example, in aspects that use a polymerase chain reaction (PCR) configuration. Formats that utilize two species of attached primer are often referred to as bridge amplification because double stranded amplicons form a bridge-like structure between the two attached primers that flank the template sequence that has been copied. Exemplary reagents and conditions that can be used for bridge amplification are described, for example, in U.S. Pat. Nos. 5,641,658 or 7,115,400; U.S. Patent Pub. Nos. 2002/0055100 A1, 2004/0096853 A1, 2004/0002090 A1, 2007/0128624 A1 or 2008/0009420 A1, each of which is incorporated herein by reference in its entirety. Amplificaiton, for example via PCR, can also be carried out with one of the amplification primers attached to the surface and the second primer in solution. An exemplary format that uses a combination of one solid phase-attached primer and a solution phase primer is known as primer walking and can be carried out as described in U.S. Pat. No. 9,476,080, which is incorporated herein by reference in its entirety. Another example is emulsion PCR which can be carried out as described, for example, in Dressman et al., *Proc. Natl. Acad. Sci. USA* 100:8817-8822 (2003), WO 05/010145, or U.S. Patent App. Pub. Nos. 2005/0130173 A1 or 2005/0064460 A1, each of which is incorporated herein by reference in its entirety.

RCA techniques can be used in a method set forth herein. Exemplary reagents that can be used in an RCA reaction and principles by which RCA produces amplicons are described, for example, in Lizardi et al., *Nat. Genet.* 19:225-232 (1998) or US Pat. App. Pub. No. 2007/0099208 A1, each of which is incorporated herein by reference in its entirety. Primers used for RCA can be in solution or attached to a surface in a flow cell.

MDA techniques can also be used in a method of the present disclosure. Some reagents and useful conditions for MDA are described, for example, in Dean et al., *Proc Natl. Acad. Sci. USA* 99:5261-66 (2002); Lage et al., *Genome Research* 13:294-307 (2003); Walker et al., *Molecular Methods for Virus Detection,* Academic Press, Inc., 1995; Walker et al., *Nucl. Acids Res.* 20:1691-96 (1992); or U.S. Pat. Nos. 5,455,166; 5,130,238; or 6,214,587, each of which is incorporated herein by reference in its entirety. Primers used for MDA can be in solution or attached to a surface in a vessel.

In particular aspects, a combination of the above-exemplified amplification techniques can be used. For example, RCA and MDA can be used in a combination wherein RCA is used to generate a concatemeric amplicon in solution (e.g., using solution-phase primers). The amplicon can then be used as a template for MDA using primers that are attached to a surface in a vessel. In this example, amplicons produced after the combined RCA and MDA steps will be attached in the vessel. The amplicons will generally contain concatemeric repeats of a target nucleotide sequence.

Nucleic acid templates that are used in a method or composition herein can be DNA such as genomic DNA, synthetic DNA, amplified DNA, complementary DNA (cDNA) or the like. RNA can also be used such as mRNA, ribosomal RNA, tRNA or the like. Nucleic acid analogs can also be used as templates herein. Thus, a mixture of nucleic acids used herein can be derived from a biological source, synthetic source or amplification product. Primers used herein can be DNA, RNA or analogs thereof Exemplary organisms from which nucleic acids can be derived include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *dictyostelium discoideum*; a fungi such as *pneumocystis carinii, Takifugu rubripes*, yeast, *Saccharamoyces cerevisiae* or *Schizosaccharomyces pombe*; or a *plasmodium falciparum*. Nucleic acids can also be derived from a prokaryote such as a bacterium, *Escherichia coli, staphylococci* or *mycoplasma pneumoniae;* an archae; a virus such as Hepatitis C virus or human immunodeficiency virus; or a viroid. Nucleic acids can be derived from a homogeneous culture or population of the above organisms or alternatively from a collection of several different organisms, for example, in a community or ecosystem. Nucleic acids can be isolated using methods known in the art including, for example, those described in Sambrook et al., *Molecular Cloning: A Laboratory Manual, 3rd edition,* Cold Spring Harbor Laboratory, New York (2001) or in Ausubel et al., *Current Protocols in Molecular Biology,* John Wiley and Sons, Baltimore, Md. (1998), each of which is incorporated by reference in its entirety.

A template nucleic acid can be obtained from a preparative method such as genome isolation, genome fragmentation, gene cloning and/or amplification. The template can be obtained from an amplification technique such as polymerase chain reaction (PCR), rolling circle amplification (RCA), multiple displacement amplification (MDA) or the like. Exemplary methods for isolating, amplifying and fragmenting nucleic acids to produce templates for analysis on an array are set forth in U.S. Pat. Nos. 6,355,431 or 9,045,796, each of which is incorporated herein by reference in its entirety. Amplification can also be carried out using a method set forth in Sambrook et al., *Molecular Cloning: A Laboratory Manual, 3rd edition*, Cold Spring Harbor Laboratory, New York (2001) or in Ausubel et al., *Current Protocols in Molecular Biology,* John Wiley and Sons, Baltimore, Md. (1998), each of which is incorporated herein by reference in its entirety.

In the context of binding reactions that involve multiple components (e.g., a receptor and a ligand), one or more components can harbor a detectable label. This is true for systems that involve formation and detection or monitoring of complexes resulting from binding of two or more components, where at least one of the components harbors a detectable label, and where the complex is in dynamic equilibrium with its chemical surroundings. Optionally, signal produced by the detectable label is substantially uniform whether or not the labeled component is part of an immobilized complex (e.g., a ternary complex) or free in solution.

Different detectable labels can be used in accordance with the disclosed technique. Optionally, the detectable label is a fluorescent label, such as an exogenous fluorescent label. Optionally, the detectable label is a Raman active label.

Generally speaking, the disclosed techniques do not share restrictions on detectable labels that characterize certain other techniques used in the DNA sequencing field. For example, there is no requirement for a label (e.g., a FRET partner) to be present on the polymerase or primed template nucleic acid. Indeed, in certain aspects the polymerase is unlabeled, or does not generate any signal used for identifying cognate or non-cognate nucleotide. Exemplary techniques for detecting ternary complexes and performing sequencing reactions without exogenous labels are set forth in references set forth herein in the context of Sequencing By Binding™ techniques and in US Pat. App. Pub. Nos. 2017/0022553A1 or 2017/0191125 A1, each of which is incorporated herein by reference in its entirety. The polymerase preferably does not transfer energy to the labeled nucleotide to render it detectable by the detection apparatus used for carrying out the technique. The label or dye of the detectable nucleotides employed in the procedure preferably is not an intercalating dye (e.g., as disclosed in U.S. Pat. No. 8,399,196), that changes its signal-generating properties (e.g., fluorescent output) upon binding DNA. As well, the label or dye present on the labeled nucleotide need not be a conformationally sensitive dye that changes spectral properties when it is the cognate nucleotide present in a ternary complex.

Stabilizing fluids can be used to reduce background signal in a method set forth herein. Reducing the solution-phase concentration of one or more of the constituents of a reversible or "transient" complex that is in dynamic equilibrium with its chemical environment can lead to dissociation and loss of the complex. For example, washing immobilized ternary complexes with nucleotide-free and polymerase-free aqueous examination buffer to deplete non-complexed labeled reagents from the surrounding solution desirably can reduce background signal to permit detection of specific complexes, but undesirably may impose limits or requirements on the timing of the detection, or may require undesirably complicated data processing to identify a cognate ligand. Commonly assigned U.S. patent application Ser. No. 15/581,828 published as US Pat. App. Pub. No. 2017/0314064 A1 (the entire disclosure of which is incorporated by reference in its entirety herein) details the phenomenon of ternary complex destabilization and describes how destabilization of the ternary complex can be used to make cognate nucleotide identification. It would be desirable to further improve reliability of detection assays for receptor-ligand interactions, particularly those employing detectably labeled (e.g., fluorescently labeled) components of the complex, by stabilizing ternary complexes, thereby enhancing signal-to-background ratios in a manner that facilitates detection of the complexes over an extended period. Stabilizing fluids in accordance with the disclosure can be used for this purpose. As confirmed by the working Examples herein, stabilizing fluids in accordance with the disclosure can be used with Sequencing By Binding™ procedures employing either labeled nucleotides or labeled polymerases.

Stabilizing fluids useful for simultaneously removing soluble components of a complex from the vicinity of an immobilized complex, and for stabilizing the complex against dissociation can be defined by certain chemical features or characteristics. Preferred stabilizing fluids exhibit either substantially no capacity, or only a sparing capacity to solubilize the detectably labeled constituent (e.g., labeled nucleotide or labeled polymerase) of the complex that is to be detected. Thus, if a ternary complex that is to be detected includes an immobilized primed template nucleic acid molecule, then the use of conditions wherein the labeled nucleotide is insoluble, or only sparingly soluble (i.e., "substantially insoluble") in the stabilizing fluid can be beneficial. When this is the case, the stabilizing fluid can at least partially displace or replace solution-phase nucleotide and polymerase in contact with an immobilized ternary complex without promoting dissociation of that complex. Preferably, this displacement or replacement (whether partial or complete) occurs within a flow cell, and is effected by flowing the stabilizing fluid into and through a flow cell containing the immobilized ternary complex to be detected. Generally speaking, any volume of the stabilizing fluid will be unavailable for partitioning of the labeled constituent(s) of the immobilized ternary complex. This effectively stabilizes the complex by inhibiting or preventing its dissociation. At the same time, non-complexed polymerase and nucleotide remaining free in solution can be removed from contact with the complex by displacement with the stabilizing fluid.

Examples of stabilizing fluids in which nucleotides (e.g., labeled nucleotides) and polymerases (e.g., labeled polymerases) are substantially insoluble include, without limitation: mineral oils or paraffin oils (e.g., mixtures of higher alkanes having 9 or more carbons); purified higher alkanes (e.g., decane); silicone oil (e.g., 100% silicone oil); perfluorocarbons (e.g., Fluorinert™ available from the 3M Company, MN); ethanol (e.g., 100% or about 70% ethanol); isopropanol (e.g., 100%, or 80% isopropanol in a buffered aqueous solution); 2-butanol (soluble in 12 parts water); and even a gas or air.

Stabilizing fluids can be either water-miscible (e.g., ethanol, isopropanol, methanol, propanol etc.) or water-immiscible (e.g., mineral oil, silicone oil, air, etc.) fluids, as long as the detectably labeled constituent of the ternary complex does not substantially partition or distribute from the immobilized complex into the stabilizing fluid used in the imaging wash step. In some aspects, a stabilizing fluid may have low solubility in an aqueous fluid but the amount of stabilizing fluid used is oversaturating such that a substantial volume of the stabilizing fluid does not dissolve in the aqueous fluid. Exemplary solvents that have low solubility in aqueous fluids include, but are not limited to, toluene, benzene, xylene, butanol, pentanol, hexanol and heptanol. References herein to use of a stabilizing fluid that is immiscible in water or an aqueous fluid will be understood to include, for example, the use of an amount of stabilizing fluid that yields a volume of stabilizing fluid that is immiscible in water or in the aqueous fluid. As such, a stabilizing fluid and an aqueous fluid can form separate fluid phases within a vessel such as a flow cell.

In accordance with aspects of the imaging wash techniques set forth herein, the labeled constituent (e.g., labeled nucleotides or labeled polymerases) or the complex to be detected preferably is either insoluble or only sparingly soluble (i.e., substantially insoluble) in the stabilizing fluid. This can be the case for water-miscible and water-immiscible stabilizing fluids. For example, the polymerase and cognate nucleotide that form a ternary complex at a feature that includes an immobilized primed template nucleic acid molecule are preferably soluble in the stabilizing fluid at a level that is less than 0.01, more preferably less than 0.001, and yet still more preferably less than 0.0001 of the solubility in an examination buffer used for providing the polymerase and nucleotide to the immobilized primed template nucleic acid molecule to assemble the ternary complex.

Expressed in terms of a distribution ratio quantifying the equilibrium concentrations of either labeled nucleotides or labeled polymerases in a water-immiscible stabilizing fluid and an aqueous examination buffer containing these components, the ratio value (D) preferably is different from 1.0 (i.e., where the labeled species would distribute equally), so that logD would be zero. More preferably, the labeled component(s) are very weakly or sparingly soluble (or even insoluble) in the water-immiscible stabilizing fluid, and highly soluble in an examination buffer solution so that the ratio of concentrations at equilibrium (i.e., stabilizing fluid concentration/examination buffer concentration) in a separated mixture of the two is less than 0.01, more preferably less than 0.001, and yet still more preferably less than 0.0001 of the level in an examination buffer used for providing the polymerase and nucleotide. Optionally, solubility of labeled polymerase or labeled nucleotide in the water-immiscible stabilizing fluid is undetectable (i.e., the labeled component is soluble in the examination buffer and completely insoluble in the stabilizing fluid).

To maintain stability of complexes (e.g., ternary complexes) which are in dynamic equilibrium with an aqueous environment within a flow cell, the stabilizing fluid can be substantially free of polymerase and/or nucleotide. This can avoid exchange of the labeled components of ternary complexes that are to be detected. This follows from the dynamic nature of ternary complexes that are detected using a Sequencing By Binding™ platform.

Procedures employing either detectably labeled polymerases or detectably labeled nucleotides can benefit from techniques that enhance signal-to-background ratios when detection of the label indicates the presence or identity of the nucleotide. This is especially the case for procedures employing labeled nucleotides (e.g., fluorescently labeled nucleotide analogs) for the reasons given above. Large excesses of signal-producing component (i.e., labeled nucleotide) can confound detection of signal arising from ternary complexes as the result of high background signals. High background signals can result from either non-complexed fluorescent nucleotides or fluorescent polymerase that remain in the solution phase at the time the fluorescent signal is detected or measured.

As discussed elsewhere herein, aqueous wash steps can sometimes undesirably promote dissociation of multicomponent complexes (e.g., ternary complexes) that are to be detected. While this phenomenon can be exploited for identifying cognate nucleotides by monitoring ternary complex destabilization, there also can be problems with signal loss due to the dynamic nature of the complex being detected. It was discovered that transient binding assays employing labeled nucleotides or labeled polymerases could experience compromised signal-to-background readings as the result of high non-specific signals (e.g., fluorescent signals); and that removing non-complexed labeled reagents using a standard wash step could promote signal loss due to the dynamic nature of the ternary complex.

This heretofore unappreciated combination of issues observed for a Sequencing By Binding™ platform was solved using a "flush" or "wash" step to remove non-complexed labeled reagents from the feature or site monitored for ternary complex formation (e.g., within a flow cell or other reaction chamber or vessel), where the step employed a fluid reagent (e.g., a non-aqueous fluid reagent) that was immiscible with the fluid containing the nucleotide, polymerase and immobilized primed template nucleic acid molecule that combined to form the ternary complex.

Use of an imaging wash in the flush step can advantageously reduce the magnitude of optical signals arising from labeled components (e.g., fluorescent nucleotides or fluorescent polymerases) remaining free in the solution phase (i.e., non-complexed labeled nucleotide). For example, excess cognate nucleotide harboring a fluorescent label and remaining in the bulk solution phase within a flow cell can generate an optical signal that obscures the fluorescent signal arising from cognate nucleotide present in ternary complexes immobilized to a surface. Because ternary complexes that form without chemical incorporation in the Sequencing By Binding™ workflow are in a dynamic equilibrium (i.e., where rates of formation and dissociation are balanced), flushing or washing the flow cell with an aqueous solution devoid of polymerase and/or cognate nucleotide to remove non-complexed nucleotide could promote undesirably rapid signal decay of ternary complexes containing labeled nucleotide. Methods set forth herein can be used to reduce signal arising from non-complexed fluorescent nucleotides while substantially maintaining the integrity of ternary complexes, thereby resolving this dilemma.

Advantageously, and surprisingly, ternary complexes that included the polymerase and labeled cognate nucleotide complexed with immobilized primed template nucleic acid remained highly stable in the presence of a non-aqueous fluid. Ternary complexes remained substantially intact and were not substantially destabilized during a non-aqueous flush step. This permitted detection of ternary complexes during the imaging wash step, when signal-to-background ratios were favorable for cognate nucleotide identification.

In certain preferred approaches, a stabilizing fluid can be immiscible with the aqueous examination solution that includes polymerase and labeled nucleotide. The immiscible fluid can be an organic reagent (e.g., an oil, such as a paraffin oil), inorganic reagent (e.g., silicone oil), or a gas (e.g., an inert gas such as argon or nitrogen, or a mixed gas such as air). Each of these categories of reagent has been used with good results.

EXAMPLES

The following Examples illustrate the simultaneous reduction of undesirable background signal (e.g., fluorescent background signal) and stabilization of ternary complexes immobilized to a solid support in a Sequencing By Binding™ workflow. The technique was shown to improve results obtained in Sequencing By Binding™ assays employing either detectably labeled nucleotides or detectably labeled polymerases. More generally, the method can be used to enhance detection of specific interactions between different components of a multi-component complex, with application to systems employing one or more detectably labeled components. Use of the technique obviates potential problems arising from reduced signal-to-background ratios due to high levels of non-complexed reagents remaining in the solution phase, where the reduced ratios can mask proper cognate nucleotide identification.

It was discovered during development of the present technique that the benefit of using high concentrations of detectably labeled components to drive formation of specific complexes was offset by high background signals resulting from non-complexed labeled reagents remaining in solution. The fact that nucleotide concentrations typically far exceed polymerase concentrations in Sequencing By Binding™ assays makes certain procedures employing labeled nucleotides particularly susceptible to this issue. Moreover, the dynamic nature of the ternary complex (e.g., where the complex is in a reversible state of formation and dissociation) complicates the situation when conventional reagent wash steps are performed to remove non-complexed reagents from the system. This is because reversible complexes can dissociate when components needed for maintenance (e.g., nucleotide and/or polymerase) are removed from the system. When the rate of dissociation is significant, the complex can be dissociated completely before it can be detected.

Accordingly, two technical issues impact clear detection of multi-component complexes when using components that include detectable labels. First, signals originating from the labeled component can obscure detection of specific complexes due to high background signals (e.g., fluorescent signals arising from non-complexed fluorescent nucleotides or fluorescent polymerases). Second, washing to remove one or more of the labeled components from the system can promote dissolution of complexes that are to be detected. Both issues were addressed by simultaneously stabilizing ternary complexes and removing non-complexed reagents (e.g., excess labeled polymerase or nucleotide remaining in solution) from the binding reaction mixture. This can be accomplished by immobilizing the ternary complex to a solid support, and then flushing the system using a stabilizing fluid in which the labeled reagent(s) are substantially insoluble. Complex-specific signals can then be detected, monitored, and/or quantified during this imaging wash step before any other fluorescent reagent is introduced into the system (e.g., by flowing through a flow cell). By this approach, components of preformed multicomponent complexes cannot substantially partition into the stabilizing fluid used in the flush step, and so association of the different components can be maintained. While not wishing to be limited by any particular theory of operation, one possibility is that multicomponent complexes can be precipitated in place with the same result as though integrity of the complex was maintained. Indeed, signal associated with immobilized complexes can be highly stable and can remain detectable over the course of 10 seconds, 30 seconds, and even at least 10 minutes. These stability ranges can easily exceed the time needed to make a measurement that would detect and/or identify the labeled component of the complex.

The following Examples show how an imaging wash with a stabilizing fluid could be used to remove non-complexed constituents of multicomponent complexes, while simultaneously stabilizing immobilized complexes. Detectability of the complexes over extended periods was improved as a consequence. Moreover, better-quality sequencing results were obtained in Sequencing By Binding™ procedures when an imaging wash employing a stabilizing fluid was included in the workflow.

Example 1 illustrates the use of a stabilizing fluid wash or flush following a ternary complex formation step that employed fluorescently labeled nucleotides. Labeled nucleotide analogs and unlabeled polymerase were used to form ternary complexes with primed template nucleic acids immobilized to beads in a flow cell. Nucleotide analogs included a fluorescent moiety that did not substantially change optical properties (e.g., excitation or emission) in the presence of polymerase and/or primed template nucleic acid. Results confirmed that, unlike an aqueous wash step that did not stabilize complexes, the stabilizing fluid substantially preserved integrity of ternary complexes over extended periods. The stabilizing fluid in this illustration was an alkane hydrocarbon that was not miscible with water. Labeled ternary complexes were detected during the imaging wash step.

Example 1

Stabilizing Flush Reduces Background Signal and Stabilizes Ternary Complexes: Labeled Nucleotide Platform Flow cells containing immobilized microbeads harboring single-stranded template nucleic acids hybridized to sequencing primers were obtained by conventional laboratory procedures familiar to those having an ordinary level of skill in the art. Four populations of beads were included in the procedure, with each bead type harboring a different primed template nucleic acid. The flow cell was first equilibrated with a pre-incorporation solution that included AMPSO buffer (about pH 9.0), 50 mM KC1, 10 mM (NH4)2SO4, 0.1% Triton X-100 (trademark of Dow Chemical Company) nonionic detergent, and 0.1% hydroxylamine to maintain integrity of reversible terminator nucleotides used in a subsequent step. Next, the flow cell was equilibrated with a solution that included four reversible terminator nucleotides, and that consisted of the pre-incorporation solution supplemented with 10 U/ml Therminator DNA polymerase (New England BioLabs), aminoxy (i.e., 3'-$ONH_2$) reversible terminator nucleotides (dATP, dGTP, dCTP and dTTP), and 5 mM $MgCl_2$ to incorporate a single reversible terminator nucleotide at the 3'-end of each different primed template nucleic acid. This blocked the primers with a reversible terminator nucleotide that precluded subsequent nucleotide incorporation. The flow cell was then equilibrated with the pre-incorporation solution to remove residual components of the incorporation reaction. Next, an examination solution that included a fluorescent dGTP nucleotide analog was flowed into the flow cell and allowed to stand for a period of 30 seconds, during which time ternary complexes formed on appropriate beads (i.e., the beads for which dGTP was the next correct nucleotide). The examination solution consisted of the pre-incorporation solution supplemented with 400 nM Cy5 base-labeled dGTP nucleotide analog, 10 U/ml Therminator polymerase, and an optional source of catalytic metal ion (i.e., 10 mM $MgCl_2$). Despite the presence of the catalytic metal ion, the nucleotide analog could not incorporate into the 3'-blocked primer. Examination solution containing the polymerase and labeled nucleotide was next replaced either by flowing into the flow cell imaging wash reagents that were either: (a) the pre-incorporation solution that did not contain either the polymerase or nucleotide; or (b) 100% decane. Here the pre-incorporation solution represented an aqueous solution in which polymerase and nucleotide were soluble, while decane represented a non-aqueous reagent in which polymerase and nucleotide were not soluble. Once flowed into the flow cell, the imaging wash reagents remained in contact with the immobilized beads without further flow. Imaging of beads under each condition was performed every second for a period of one minute, where exposures were one second each. Three regions of interest corresponding to different beads were selected, and quantified images of the beads as a function of time were background subtracted (i.e., signal from beads that remained non-fluorescent were used for the subtraction). Notably, because the light source used for exciting the nucleotide-linked fluorophore was continuously on during the procedure, photobleaching (i.e., emission signal decreases with increasing time of exposure to the excitation wavelength) of the fluorescent dye moiety was to be expected.

Results presented in FIG. 1 illustrated dramatic differences in the stabilities of ternary complexes incubated in the different imaging wash reagents. Data plotted in the figure was normalized to the first image in each series. Decane-stabilized ternary complexes exhibited about 20% reduced signal after 20 seconds. In comparison, ternary complexes incubated in the pre-incorporation solution lost about 80% of the fluorescent signal after the same period. Significantly, signal loss in the trial carried out using decane as the imaging wash reagent was predominantly an artifact of photobleaching the Cy5 fluorophore rather than decomposition of the ternary complex. Extended photoirradiation was only used in the procedure to capture the time course data, and alternatively imaging the decane trial only at the start and finish of the one-minute incubation period would show substantially less signal loss. Conversely, the rapid signal loss observed for the trial employing the aqueous buffer in which polymerase and nucleotide were soluble was due to instability and dissociation or decomposition of ternary complexes.

Example 2 illustrates how the model stabilizing fluid described in Example 1 could be used to improve detection of binding interactions. The system used in this demonstration employed a Sequencing By Binding™ protocol to generate nucleic acid sequencing data. The stabilizing fluid simultaneously reduced background fluorescence attributed to non-complexed fluorescent nucleotide analogs, and stabilized ternary complexes that included a primed template nucleic acid, a polymerase, and a fluorescently labeled cognate nucleotide analog. Non-specific fluorescent background signal was reduced by removing non-complexed labeled binding components from a flow cell system. The procedure employed fluorescently labeled nucleotide analogs and unlabeled polymerase to form ternary complexes with primed template nucleic acids immobilized to beads contained within a flow cell. Components of the ternary complexes interacted in a reversible fashion, where the complexes were in dynamic equilibrium with their chemical environments. The detectable label attached to the nucleotide analogs included a fluorescent moiety that did not substantially change optical properties (e.g., excitation or emission) in the presence of polymerase and/or primed template nucleic acid. Energy transfer to or from another chemical moiety was not required for success of the procedure. Results presented below confirmed that the stabilizing fluid substantially preserved the integrity of ternary complexes over the course of at least 30 seconds. Similar procedures showed that ternary complexes were maintained stable for at least 5 minutes, and for at least 10 minutes. Correct base calls were made using only fluorescent imaging data acquired during the stabilizing fluid flush (e.g., the "imaging wash" step). While processing of ternary complexes prepared from synthetic oligonucleotides immobilized to beads is described here, similar procedures can be carried out using template strands synthesized in situ within a flow cell (e.g., using a rolling circle amplification protocol). Again, an organic oil (i.e., a purified higher alkane) served as the stabilizing fluid in this Example. However, good results also have been achieved using mineral oils, paraffin oils, inorganic silicone oils, perfluorocarbons, ethanol and aqueous ethanol solutions, isopropanol and aqueous isopropanol solutions, 2-butanol, air, etc. Neither the nucleotide nor the polymerase used for assembling ternary complexes could substantially dissolve or partition into any of these reagents.

Example 2

Sequencing Procedure Employing a Stabilizing Fluid that Simultaneously Stabilized Ternary Complexes and Reduced Background Signal Beads harboring synthetic oligonucleotides hybridized to sequencing primers (i.e., primed template nucleic acid molecules) were used for conducting Sequencing By Binding™ reactions with a fluorescently labeled nucleotide analog, where the examination step included an imaging wash to remove or displace from a flow cell any non-complexed polymerase and nucleotide prior to fluorescent image capture. Imaging washes used either a stabilizing fluid (e.g., n-decane) or the aqueous pre-incorporation solution of Example 1. Streptavidin-coated beads bound to an inner surface of a flow cell harbored biotinylated template DNA that was hybridized to a complementary oligonucleotide primer. Enzymatic incorporation of a cognate nucleotide with a 3'-$ONH_2$ reversible terminator moiety into the primer strand was carried out essentially as described under Example 1 to result in a reversibly terminated (i.e., "blocked") primed template nucleic acid molecule. Examination reagent solutions used in the procedure included pre-incorporation solution supplemented with either 400 nM Cy5 base-labeled dATP, 200 nM Cy5 base-labeled dGTP, 400 nM Cy5 base-labeled dCTP, or 800 nM Cy5 base-labeled dTTP. Four separate examination buffers that included a polymerase and a single nucleotide labeled on its base with a Cy5 fluorescent moiety (i.e., Cy5-dATP, Cy5-dGTP, Cy5-dCTP, or Cy5-dTTP) were introduced into the flow cell one after the other to permit formation of ternary complexes with the reversibly terminated primed template nucleic acid when the nucleotide was the next correct nucleotide. Each ternary complex included an immobilized blocked primed template nucleic acid molecule, a polymerase, and a fluorescently labeled cognate nucleotide. Polymerase used in the procedure was the native Therminator DNA polymerase (New England BioLabs) that retained catalytic activity. Following introduction of each different examination buffer into the flow cell to permit formation of ternary complexes, the flow cell was flushed completely with either decane or the aqueous pre-incorporation of Example 1 that did not contain either polymerase or nucleotide. This removed non-complexed fluorescent nucleotide analogs remaining free in solution within the flow cell. An imaging step measured fluorescent signal associated with the beads during the wash step, and before any other reagent was flowed into the flow cell. After investigating ternary complex formation using each of four different nucleotides, the polymerase and cognate nucleotide were stripped from the blocked primed template nucleic acid by washing the flow cell with an EDTA-containing high-salt (e.g., 1M NaCl) buffer. The blocking group on the primer was then removed using a cleavage or deblocking solution that included sodium acetate buffer and $NaNO_2$. The next cognate nucleotide containing a reversible terminator blocking group was incorporated as described above. This advanced or lengthened the primer by a single nucleotide. Thereafter, binding interaction of the blocked primed template nucleic acid molecule with polymerase and the next test nucleotide was investigated by repeating the procedure and imaging fluorescent signals during the wash steps. Polymerase used in this procedure did not include any exogenous fluorescent label that was detected to make the cognate nucleotide identification (i.e., polymerase was unlabeled). Interrogation of blocked primed template nucleic acid molecules, including cycles of examination, fluorescent imaging during wash steps, de-blocking, and incorporation of unlabeled reversible terminator nucleotides was repeated for 11 complete cycles to determine the identity or sequence of consecutive cognate nucleotides. Images were captured 10 seconds after flowing decane into the flow cell to replace the solution containing polymerase and nucleotide. Notably, essentially identical procedures that extended the decane exposure time to 5 minutes or 10 minutes gave results substantially identical to the procedure employing the 10 second exposure period. Use of a non-catalytic metal ion that inhibits incorporation alternatively can be used in place of the blocked primed template nucleic acid molecule to stabilize ternary complexes and preclude or prevent polymerase-mediated nucleotide incorporation. An engineered polymerase incapable of catalyzing phosphodiester bond formation also can be used to stabilize ternary complexes and prevent nucleotide incorporation.

Figure 2B:
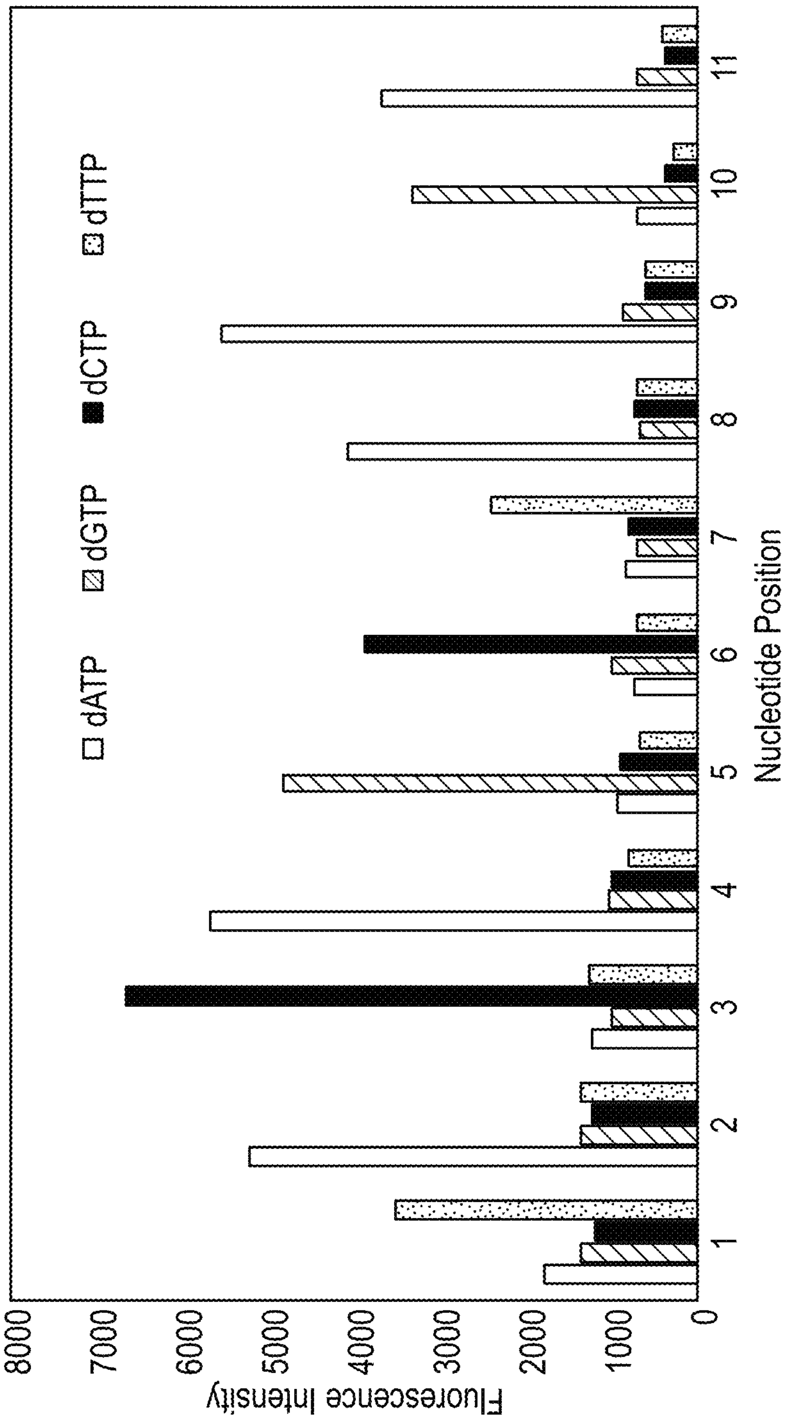
FIGS. 2A-2B show results from a labeled nucleotide sequencing procedure employing decane as a stabilizing fluid during an imaging wash step.
Figure 2A:
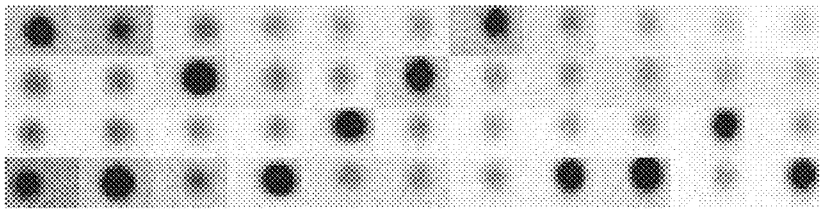

Results from these procedures indicated that an imaging wash with a stabilizing fluid could be used to reduce fluorescent background while maintaining fluorescent signal specific for ternary complex formation. Signal specific for ternary complexes was not detected for control reactions conducted using the aqueous pre-incorporation solution as the imaging wash. This was because ternary complexes dissociated to the point of being undetectable in the aqueous imaging wash solution before images could be captured. This was especially problematic for the labeled dTTP nucleotide, which seemed to be lost from the ternary complex immediately upon exposure to wash solutions in which the nucleotide was soluble. In contrast, FIG. 2A shows images of a single bead during the imaging wash step performed using decane as the stabilizing fluid. Each row of four images represents a complete cycle of examination with four different fluorescently labeled nucleotides (i.e., in order: Cy5-dATP, Cy5-dGTP, Cy5-dCTP, and Cy5-dTTP). Consecutive rows represent consecutive nucleotide positions being examined, where a reversible terminator moiety was removed and a subsequent reversible terminator nucleotide incorporated to advance the primer by a single nucleotide. Quantitation of the image intensities is graphically presented in FIG. 2B. Correct base calls corresponded to the highest magnitude signal from each set of four nucleotides for each complete examination cycle. Again, all fluorescent readings were acquired during the imaging wash steps when the flow cell contained the stabilizing fluid (i.e., decane).

Following are descriptions showing how a gas, such as air, could be used as an alternative stabilizing fluid for flushing or washing immobilized ternary complexes to improve detectability of the complexes. Again, constituents or components of the complexes to be detected did not dissolve or partition into the stabilizing fluid, and so the transient or reversible complexes were maintained in a stable configuration during the imaging wash step.

Example 3 further illustrates how a stabilizing fluid simultaneously reduced non-specific background signal and stabilized ternary complexes in a flow cell system. The procedure employed fluorescently labeled polymerase and native nucleotides to form ternary complexes with primed template nucleic acid molecules. Good results also have been achieved using fluorescently labeled nucleotides and unlabeled polymerase to form the ternary complexes. Primed template nucleic acids included either nucleic acid amplification products immobilized to a surface within a flow cell, or synthetic oligonucleotides that were immobilized to beads contained within flow cells. Air served as the stabilizing fluid in this Example. The excellent discrimination results presented below indicated that correct base calls could be made using only the fluorescent imaging results acquired during the imaging wash step (e.g., after air displaced examination buffer from within a flow cell).

Example 3

Use of a Stabilizing Fluid to Simultaneously Reduce Background Signal and Stabilize Ternary Complexes: Labeled Polymerase Platform Beads harboring synthetic primed template nucleic acid molecules were used for conducting Sequencing By Binding™ reactions with a fluorescently labeled polymerase, where the examination step included either an "air wash" or an aqueous buffer wash to remove non-complexed polymerase and nucleotide prior to fluorescent image capture. Streptavidin-coated beads covalently bound to an inner surface of a flow cell harbored biotinylated template DNA hybridized to a complementary oligonucleotide primer. Enzymatic incorporation into the primer strand of a single nucleotide having a 3'-$ONH_2$ reversible terminator moiety resulted in a reversibly terminated (i.e., "blocked") primed template nucleic acid molecule for use in a subsequent examination step. An examination buffer that included a fluorescently labeled polymerase, a single native test nucleotide, and a non-catalytic metal ion (i.e., $SrCl_2$) was introduced into the flow cell to permit formation of ternary complexes when the nucleotide was the next correct nucleotide. Notably, use of either a blocked primer or a non-catalytic metal ion that inhibits incorporation is sufficient to stabilize ternary complex formation and preclude or prevent polymerase-mediated nucleotide incorporation (i.e., it is unnecessary to include both). Alternatively, an engineered polymerase incapable of catalyzing magnesium-dependent phosphodiester bond formation can instead be used to stabilize ternary complexes and prevent nucleotide incorporation. An exemplary crippled DNA polymerase useful in this regard is described in commonly assigned U.S. patent application Ser. No. 15/581,822 published as US Pat. App. Pub. No. 2017/0314072 A1, the disclosure of which is incorporated by reference in its entirety. In the present procedure, however, the polymerase was a Bsu-derived polymerase that retained catalytic activity, and that was covalently attached to a Cy5 fluorophore. Next, the flow cell was flushed completely with either: (a) air; or (b) examination buffer that omitted polymerase and nucleotide. An imaging step then captured a digital image of the flow cell containing beads under each condition. Quantitative data from the imaging steps, which were collected during the wash steps and before any other reagent contacted the immobilized beads, was used to assess the efficiency of removing fluorescent reagent that remained free in solution and not part of an immobilized ternary complex. Polymerase and nucleotide complexed with the blocked primed template nucleic acid molecule were removed by washing the flow cell with an EDTA-containing, high-salt (e.g., 1M NaCl) buffer. Thereafter, the binding interaction of the blocked primed template nucleic acid molecule with polymerase and the next test nucleotide was investigated by repeating the procedure and imaging fluorescent signals during the wash steps. After investigating ternary complex formation using each of four different nucleotides, the blocking group on the primer was removed by chemical cleavage, and the next cognate nucleotide containing a reversible terminator blocking group was incorporated. This advanced or lengthened the primer by a single nucleotide. Reversible terminator nucleotides used in this procedure did not include exogenous fluorescent labels that were detected (i.e., reversible terminator nucleotides were unlabeled). Interrogation of blocked primed template nucleic acid molecules, including cycles of nucleotide examination, fluorescent imaging during wash steps, deblocking to remove reversible terminator moieties, and incorporation of unlabeled reversible terminator nucleotides, was repeated for 40 cycles.

In a related procedure, stability of ternary complexes during an air wash within a flow cell was assessed using either beads displaying synthetic oligonucleotides that were hybridized to sequencing primers, or alternatively using DNA templates synthesized in situ by Rolling Circle Amplification and then hybridized to a sequencing primer. Immobilized beads and immobilized amplification products located at fixed positions (but not necessarily pre-determined positions) within the flow cell are sometimes referred to herein as "features." Examination buffer that included fluorescently labeled polymerase, a single nucleotide (i.e., either dATP or dCTP), and a non-catalytic metal ion (i.e., $SrCl_2$) was flowed into a flow cell to permit ternary complex formation when the nucleotide being examined was the next correct nucleotide. In this procedure, dCTP was the next correct nucleotide, while dATP served as a model incorrect nucleotide. After flushing the flow cell with air to remove the liquid contents, there was a delay of 0, 20, 40, or 60 seconds before fluorescent imaging was performed. To avoid photobleaching effects, different trials were conducted for samples subjected to the different delay times. Again, digital images of the flow cells were captured while the flow cell was filled with air that displaced the examination buffer (i.e., during the air wash), and before any subsequent reagent was introduced into the flow cell. Fluorescent signal specifically associated with different features (i.e., either beads or clusters representing individual amplification products) were determined by subtracting measured fluorescent background signal from raw fluorescent signals associated with the different features. Background signal was determined as the fluorescent signal that was not associated with immobilized beads (sometimes referred to as "off signal").

Figure 3A:
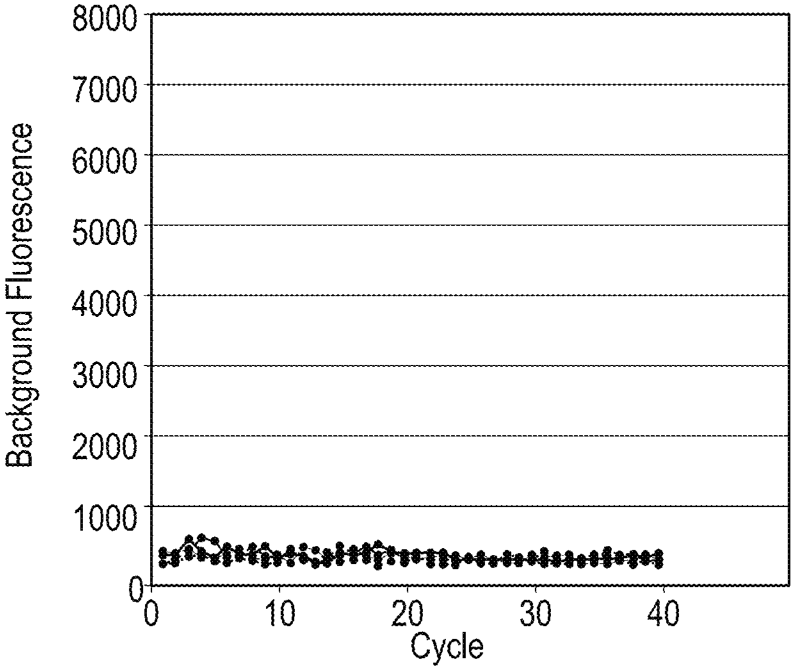
FIGS. 3A-3B show results from replicate fluorescent background determinations using different wash reagents.
Figure 3B:
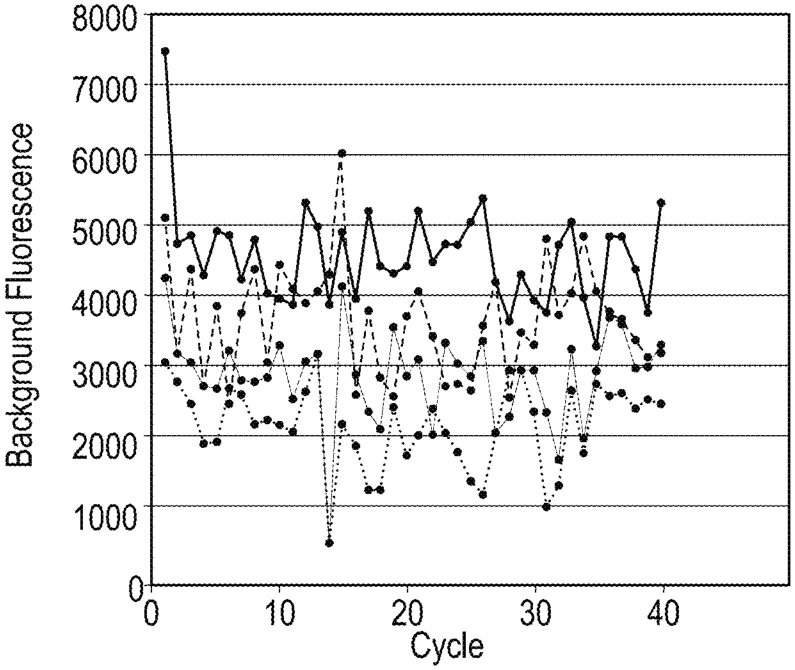
Figure 4A:
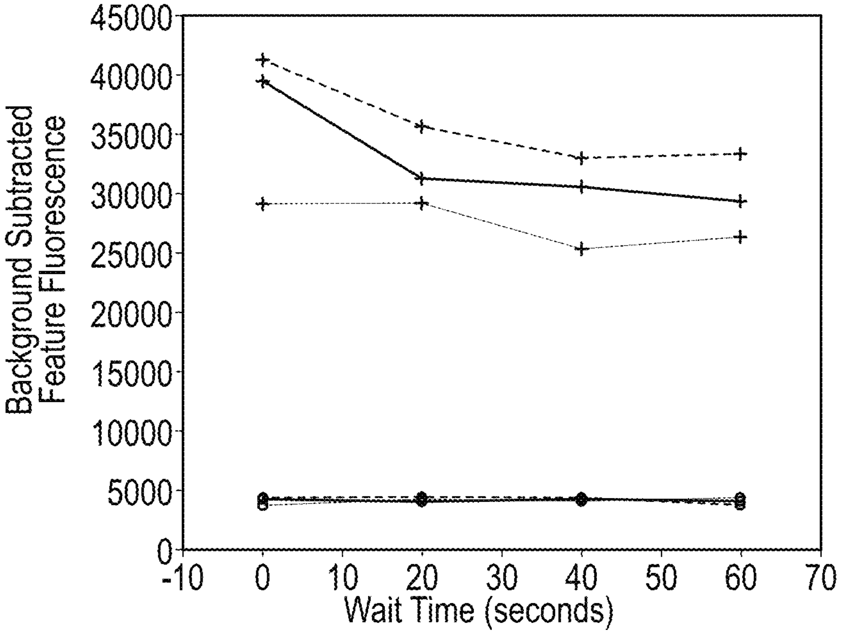
FIGS. 4A-4B show results from three replicates of background-subtracted fluorescence readings measured for nucleic acid features contacted with either cognate or non-cognate labeled nucleotide, where fluorescence data was gathered after an air flow displaced examination buffer that included nucleotide and labeled polymerase. Nucleic acid features in the procedure were either beads harboring synthetic oligonucleotides hybridized to primers (FIG. 4A), or RCA amplification products synthesized in situ and then hybridized to sequencing primers (FIG. 4B). In each of the two plots, the upper sets of three replicates correspond to results obtained using cognate nucleotides (+), while the lower sets of three replicates correspond to results obtained using non-cognate nucleotides (°).
Figure 4B:
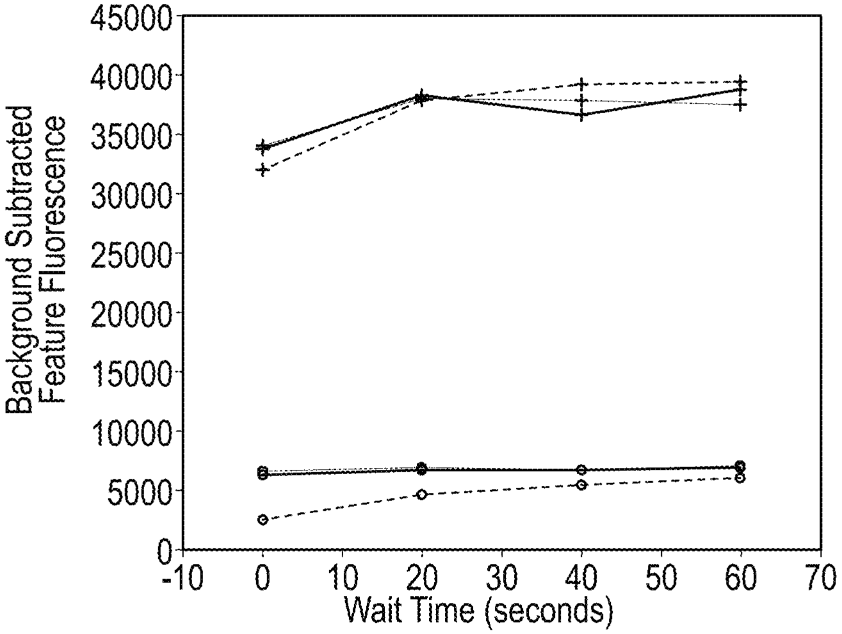

Results from these procedures indicated that an air wash could be used to reduce fluorescent background while maintaining fluorescent signal specific for ternary complex formation. In addition, the fluctuations in background fluorescence were reduced when using air as the imaging wash reagent. Reduced background fluctuations advantageously can improve sequencing accuracy and increase sequence read-length. FIGS. 3A (air wash) and 3B (aqueous buffer wash) show the fiftieth percentile of the fluorescent background signal for each of the four examined nucleotides per cycle. Inclusion of the air wash imaging step, where fluorescence data was captured following displacement of the examination buffer by air (i.e., as the wash step was taking place), reduced fluorescent background signal by about 80%-90% when compared to wash steps performed using a buffer in which polymerase and nucleotide were both soluble. FIGS. 4A and 4B, each presenting three replicates of testing using cognate and non-cognate nucleotides, show the ninetieth percentile of background-subtracted (e.g., "extracted") signal intensity. FIG. 4A presents results obtained using beads as features, and shows that extracted intensity for the cognate nucleotide was higher at all time points compared to signals measured using the non-cognate nucleotide. In this instance the ternary complex-specific signal decreased somewhat over the course of the wait period, but remained very stable for wait times of from 20-60 seconds. FIG. 4B presents results obtained using RCA products as the features, and also shows that extracted intensity for cognate nucleotide was higher at all time points compared to signals measured using the non-cognate nucleotide. In this instance, the ternary complex-specific signal remained very steady in air after displacing the polymerase- and nucleotide-containing examination buffer (i.e., during the air wash).

Taken together, these results demonstrated how an air wash step simultaneously reduced background fluorescence while stabilizing ternary complexes. Ternary complexes were stable for at least 60 seconds, and discrimination between correct and incorrect nucleotides could be carried out using air to reduce background fluorescence by removal of non-complexed fluorescent reagent after ternary complex formation but prior to fluorescent imaging. Moreover, the difference between the correct and incorrect extracted intensities remained surprisingly stable over time without compromising the ability to strip polymerase and nucleotide from ternary complexes to prepare the flow cell for the next round of cycling reactions. Notably, substantially similar results were obtained when the primed template nucleic acid included a 3'-end that was available for polymerization or blocked by the presence of a reversible terminator moiety.

A number of specific examples and aspects thereof have been described herein. Of course, a number of different aspects will suggest themselves to those having ordinary skill in the art upon review of the foregoing detailed description. Thus, the scope is to be determined upon reference to the appended claims.

What is claimed is:

1. A method of detecting an immobilized ternary complex, said method comprising the steps of:

(a) providing a vessel comprising an immobilized ternary complex in a first fluid phase, wherein the immobilized ternary complex comprises a primed template nucleic acid molecule, a first polymerase and a first test nucleotide, wherein the first fluid phase comprises nucleotides of the same type as the first test nucleotide, and wherein the first test nucleotide is in diffusional exchange with the first fluid phase;

(b) replacing at least a portion of the first fluid phase in the vessel with a second fluid phase, wherein the first test nucleotide is insoluble in the second fluid phase; and (c) detecting the immobilized ternary complex in the presence of the second fluid phase.

2. The method of claim 1, wherein the first test nucleotide comprises a detectable label and wherein step (c) comprises detecting the immobilized ternary complex in contact with the second fluid phase by detecting the detectable label.

3. The method of claim 2, wherein the detectable label comprises a fluorescent moiety.

4. The method of claim 1, wherein the first test nucleotide comprises the detectable label, and the first polymerase does not comprise any chemical moiety in energy transfer relationship with the detectable label of the first test nucleotide.

5. The method of claim 1, further comprising, after step (b), a step of destabilizing the immobilized ternary complex in the first fluid phase with the addition of the second fluid phase in the vessel, the second fluid phase removing at least a portion of the first polymerase and the first test nucleotide from contact with the immobilized primed template nucleic acid molecule.

6. The method of claim 5, further comprising, after the destabilizing step, a step of incorporating a cognate nucleotide into the primer strand of the immobilized primed template nucleic acid molecule.

7. The method of claim 6, wherein the cognate nucleotide incorporated into the primer strand of the immobilized primed template nucleic acid molecule is a reversible terminator nucleotide comprising a reversible terminator moiety.

8. The method of claim 1, wherein the immobilized primed template nucleic acid molecules of step (a) is a blocked primed template nucleic acid molecules comprising a reversible terminator moiety.

9. The method of claim 1, wherein the immobilized primed template nucleic acid molecule of step (a) is a blocked primed template nucleic acid molecule comprising a reversible terminator moiety, and wherein after the destabilizing step there are the further steps of:

cleaving the reversible terminator moiety from the blocked primed template nucleic acid molecule to result in a de-blocked primed template nucleic acid molecule; and incorporating a cognate nucleotide into the de-blocked primed template nucleic acid molecule.

10. The method of claim 9, wherein the cognate nucleotide incorporated into the de-blocked primed template nucleic acid molecule is a reversible terminator nucleotide.

11. The method of claim 10, further comprising repeating all of the steps to determine the identities of consecutive nucleotides in the immobilized primed template nucleic acid molecule.

12. The method of claim 1, wherein the immobilized primed template nucleic acid molecules are immobilized to the surface of a bead.

13. The method of claim 1, wherein the first fluid phase is a non-aqueous fluid.

14. The method of claim 13, wherein the non-aqueous fluid is a gas.

15. The method of claim 13, wherein the non-aqueous fluid is an oil.

16. The method of claim 1, wherein the first polymerase comprises a detectable label and wherein step (c) comprises detecting the immobilized ternary complex in contact with the second fluid phase by detecting the detectable label of the first polymerase.

17. The method of claim 16, wherein the detectable label comprises an exogenous fluorescent label attached to the first polymerase.

18. The method of claim 1, wherein the vessel of step (a) is a flow cell.

19. The method of claim 1, wherein the first fluid phase is a stabilizing fluid.

20. The method of claim 1, wherein the second fluid phase is a wash solution that removes the first polymerase and the first test nucleotide from contact with the immobilized primed template nucleic acid molecule.

21. The method of claim 1, wherein the second fluid phase is an aqueous fluid.

* * * * *